(12) United States Patent
Braido

(10) Patent No.: US 9,532,868 B2
(45) Date of Patent: Jan. 3, 2017

(54) COLLAPSIBLE-EXPANDABLE PROSTHETIC HEART VALVES WITH STRUCTURES FOR CLAMPING NATIVE TISSUE

(75) Inventor: Peter Nicholas Braido, Maple Grove, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 304 days.

(21) Appl. No.: 11/906,133

(22) Filed: Sep. 28, 2007

(65) Prior Publication Data

US 2014/0155997 A1    Jun. 5, 2014

(51) Int. Cl.
A61F 2/24    (2006.01)

(52) U.S. Cl.
CPC ............... *A61F 2/24* (2013.01); *A61F 2/2409* (2013.01); *A61F 2/2418* (2013.01); *A61F 2/2433* (2013.01); *A61F 2220/0008* (2013.01); *A61F 2230/005* (2013.01); *A61F 2230/0054* (2013.01); *A61F 2230/0078* (2013.01)

(58) Field of Classification Search
CPC ........ A61F 2/24; A61F 2/2418; A61F 2/2412; A61F 2/848; A61F 2002/8483; A61F 2002/8486; A61F 2/2475; A61F 2250/0039; A61F 2250/0003; A61F 2/82
USPC ............... 623/900, 2.4, 2.13, 2.1, 2.11, 2.12, 2.14,623/2.17, 1.24, 1.26, 1.36, 2.18, 2.36–2.37, 1.3; 606/1
See application file for complete search history.

(56) References Cited

U.S. PATENT DOCUMENTS

| | | |
|---|---|---|
| 3,657,744 A | 4/1972 | Ersek |
| 4,056,854 A | 11/1977 | Boretos et al. |
| 4,275,469 A | 6/1981 | Gabbay |
| RE30,912 E | 4/1982 | Hancock |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |

(Continued)

FOREIGN PATENT DOCUMENTS

| | | |
|---|---|---|
| DE | 19857887 A1 | 7/2000 |
| DE | 10121210 A1 | 11/2002 |

(Continued)

OTHER PUBLICATIONS

International Search Report (dated Mar. 12, 2009), International Preliminary Report on Patentability (dated Mar. 30, 2010), and Written Opinion (dated Mar. 28, 2010), PCT/US2008/011188.

(Continued)

*Primary Examiner* — Christian Sevilla
*Assistant Examiner* — Seema Mathew
(74) *Attorney, Agent, or Firm* — Lerner, David, Littenberg, Krumholz & Mentlik, LLP

(57) ABSTRACT

A prosthetic heart valve is designed to be circumferentially collapsible for less invasive delivery into the patient. At the implant site the valve re-expands to a larger circumferential size, i.e., the size that it has for operation as a replacement for one of the patient's native heart valves. The valve includes structures that, at the implant site, extend radially outwardly to engage tissue structures above and below the native heart valve annulus. These radially outwardly extending structures clamp the native tissue between them and thereby help to anchor the prosthetic valve at the desired location in the patient.

15 Claims, 18 Drawing Sheets

(56) References Cited

U.S. PATENT DOCUMENTS

| | | | |
|---|---|---|---|
| 5,415,667 A * | 5/1995 | Frater | 623/2.11 |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,045,576 A | 4/2000 | Starr et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,312,465 B1 | 11/2001 | Griffin et al. | |
| 6,368,348 B1 | 4/2002 | Gabbay | |
| 6,419,695 B1 | 7/2002 | Gabbay | |
| 6,454,799 B1 * | 9/2002 | Schreck | 623/2.18 |
| 6,458,153 B1 * | 10/2002 | Bailey et al. | 623/1.24 |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,462 B1 | 6/2003 | Andersen et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,652,578 B2 * | 11/2003 | Bailey et al. | 623/1.24 |
| 6,685,625 B2 | 2/2004 | Gabbay | |
| 6,712,836 B1 * | 3/2004 | Berg | A61B 17/0057 |
| | | | 606/213 |
| 6,716,244 B2 | 4/2004 | Klaco | |
| 6,719,789 B2 | 4/2004 | Cox | |
| 6,726,715 B2 * | 4/2004 | Sutherland | 623/2.1 |
| 6,730,118 B2 | 5/2004 | Spenser et al. | |
| 6,733,525 B2 * | 5/2004 | Yang et al. | 623/2.18 |
| 6,767,362 B2 * | 7/2004 | Schreck | 623/2.11 |
| 6,783,556 B1 | 8/2004 | Gabbay | |
| 6,790,229 B1 * | 9/2004 | Berreklouw | 623/2.1 |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,830,585 B1 | 12/2004 | Artof et al. | |
| 6,869,444 B2 | 3/2005 | Gabbay | |
| 6,875,231 B2 | 4/2005 | Anduiza et al. | |
| 6,893,460 B2 | 5/2005 | Spenser et al. | |
| 6,908,481 B2 | 6/2005 | Cribier | |
| 6,951,573 B1 | 10/2005 | Dilling | |
| 7,018,406 B2 | 3/2006 | Seguin et al. | |
| 7,018,408 B2 * | 3/2006 | Bailey et al. | 623/2.11 |
| 7,025,780 B2 | 4/2006 | Gabbay | |
| 7,041,132 B2 * | 5/2006 | Quijano et al. | 623/2.11 |
| 7,044,966 B2 | 5/2006 | Svanidze et al. | |
| 7,101,396 B2 * | 9/2006 | Artof et al. | 623/2.18 |
| 7,137,184 B2 | 11/2006 | Schreck | |
| 7,147,663 B1 | 12/2006 | Berg et al. | |
| 7,160,322 B2 | 1/2007 | Gabbay | |
| 7,195,641 B2 * | 3/2007 | Palmaz et al. | 623/2.18 |
| 7,198,646 B2 | 4/2007 | Figulla et al. | |
| 7,201,772 B2 | 4/2007 | Schwammenthal et al. | |
| 7,247,167 B2 | 7/2007 | Gabbay | |
| 7,252,682 B2 | 8/2007 | Seguin | |
| 7,267,686 B2 | 9/2007 | DiMatteo et al. | |
| 7,276,078 B2 | 10/2007 | Spenser et al. | |
| 7,311,730 B2 | 12/2007 | Gabbay | |
| 7,320,704 B2 | 1/2008 | Lashinski et al. | |
| 7,329,278 B2 | 2/2008 | Seguin et al. | |
| 7,331,991 B2 * | 2/2008 | Kheradvar | A61F 2/2418 |
| | | | 623/1.22 |
| 7,338,520 B2 * | 3/2008 | Bailey et al. | 623/1.24 |
| 7,374,573 B2 | 5/2008 | Gabbay | |
| 7,381,218 B2 * | 6/2008 | Schreck | 623/1.26 |
| 7,381,219 B2 | 6/2008 | Salahieh et al. | |
| 7,452,371 B2 | 11/2008 | Pavcnik et al. | |
| 7,510,572 B2 * | 3/2009 | Gabbay | 623/2.11 |
| 7,510,575 B2 | 3/2009 | Spenser et al. | |
| 7,524,331 B2 | 4/2009 | Birdsall | |
| 7,527,647 B2 * | 5/2009 | Spence | 623/2.36 |
| 7,530,995 B2 * | 5/2009 | Quijano et al. | 623/1.24 |
| 7,534,261 B2 | 5/2009 | Friedman | |
| RE40,816 E | 6/2009 | Taylor et al. | |
| 7,585,321 B2 | 9/2009 | Cribier | |
| 7,628,805 B2 | 12/2009 | Spenser et al. | |
| 7,682,390 B2 | 3/2010 | Seguin | |
| 7,708,775 B2 | 5/2010 | Rowe et al. | |
| 7,731,742 B2 | 6/2010 | Schlick et al. | |
| 7,748,389 B2 | 7/2010 | Salahieh et al. | |
| 7,780,725 B2 | 8/2010 | Haug et al. | |
| 7,799,069 B2 | 9/2010 | Bailey et al. | |
| 7,803,185 B2 | 9/2010 | Gabbay | |
| 7,824,442 B2 | 11/2010 | Salahieh et al. | |
| 7,837,727 B2 | 11/2010 | Goetz et al. | |
| 7,846,203 B2 | 12/2010 | Cribier | |
| 7,846,204 B2 | 12/2010 | Letac et al. | |
| 7,892,281 B2 | 2/2011 | Seguin et al. | |
| 7,914,569 B2 | 3/2011 | Nguyen et al. | |
| 7,959,666 B2 | 6/2011 | Salahieh et al. | |
| 7,959,672 B2 | 6/2011 | Salahieh et al. | |
| 7,972,378 B2 | 7/2011 | Tabor et al. | |
| 7,988,724 B2 | 8/2011 | Salahieh et al. | |
| 7,993,394 B2 | 8/2011 | Hariton et al. | |
| 8,016,877 B2 | 9/2011 | Seguin et al. | |
| D648,854 S | 11/2011 | Braido | |
| 8,048,153 B2 | 11/2011 | Salahieh et al. | |
| 8,052,741 B2 | 11/2011 | Bruszewski et al. | |
| 8,052,749 B2 | 11/2011 | Salahieh et al. | |
| 8,052,750 B2 | 11/2011 | Tuval et al. | |
| 8,062,355 B2 | 11/2011 | Figulla et al. | |
| 8,075,611 B2 | 12/2011 | Millwee et al. | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| 8,137,398 B2 | 3/2012 | Tuval et al. | |
| 8,142,497 B2 | 3/2012 | Friedman | |
| D660,432 S | 5/2012 | Braido | |
| D660,433 S | 5/2012 | Braido et al. | |
| D660,967 S | 5/2012 | Braido et al. | |
| 8,182,528 B2 | 5/2012 | Salahieh et al. | |
| 8,221,493 B2 | 7/2012 | Boyle et al. | |
| 8,230,717 B2 | 7/2012 | Matonick | |
| 8,231,670 B2 | 7/2012 | Salahieh et al. | |
| 8,252,051 B2 | 8/2012 | Chau et al. | |
| 8,308,798 B2 | 11/2012 | Pintor et al. | |
| 8,313,525 B2 | 11/2012 | Tuval et al. | |
| 8,323,335 B2 | 12/2012 | Rowe et al. | |
| 8,323,336 B2 | 12/2012 | Hill et al. | |
| 8,343,213 B2 | 1/2013 | Salahieh et al. | |
| 8,348,995 B2 | 1/2013 | Tuval et al. | |
| 8,348,996 B2 | 1/2013 | Tuval et al. | |
| 8,348,998 B2 | 1/2013 | Pintor et al. | |
| 8,366,769 B2 | 2/2013 | Huynh et al. | |
| 8,403,983 B2 | 3/2013 | Quadri et al. | |
| 8,408,214 B2 | 4/2013 | Spenser | |
| 8,414,643 B2 | 4/2013 | Tuval et al. | |
| 8,425,593 B2 | 4/2013 | Braido et al. | |
| 8,449,599 B2 | 5/2013 | Chau et al. | |
| 8,449,604 B2 | 5/2013 | Moaddeb et al. | |
| 8,454,686 B2 | 6/2013 | Alkhatib | |
| 8,465,540 B2 * | 6/2013 | Straubinger | A61F 2/2418 |
| | | | 623/1.24 |
| 8,500,798 B2 | 8/2013 | Rowe et al. | |
| 8,568,474 B2 | 10/2013 | Yeung et al. | |
| 8,579,962 B2 | 11/2013 | Salahieh et al. | |
| 8,579,966 B2 | 11/2013 | Seguin et al. | |
| 8,585,755 B2 | 11/2013 | Chau et al. | |
| 8,591,575 B2 | 11/2013 | Cribier | |
| 8,597,349 B2 | 12/2013 | Alkhatib | |
| 8,603,159 B2 | 12/2013 | Seguin et al. | |
| 8,603,160 B2 | 12/2013 | Salahieh et al. | |
| 8,613,765 B2 | 12/2013 | Bonhoeffer et al. | |
| 8,623,074 B2 | 1/2014 | Ryan | |

(56) References Cited

U.S. PATENT DOCUMENTS

| | | | |
|---|---|---|---|
| 8,652,204 B2 | 2/2014 | Quill et al. | |
| 8,663,322 B2 | 3/2014 | Keranen | |
| 8,668,733 B2 | 3/2014 | Haug et al. | |
| 8,685,080 B2 | 4/2014 | White | |
| 8,685,086 B2* | 4/2014 | Navia | A61F 2/2418 623/2.14 |
| 8,728,154 B2 | 5/2014 | Alkhatib | |
| 8,747,459 B2 | 6/2014 | Nguyen et al. | |
| 8,764,820 B2 | 7/2014 | Dehdashtian et al. | |
| 8,795,357 B2* | 8/2014 | Yohanan | A61F 2/2418 623/2.14 |
| 8,801,776 B2 | 8/2014 | House et al. | |
| 8,808,356 B2 | 8/2014 | Braido et al. | |
| 8,828,078 B2 | 9/2014 | Salahieh et al. | |
| 8,834,563 B2 | 9/2014 | Righini | |
| 8,840,663 B2 | 9/2014 | Salahieh et al. | |
| 8,876,894 B2 | 11/2014 | Tuval et al. | |
| 8,876,895 B2 | 11/2014 | Tuval et al. | |
| 8,940,040 B2 | 1/2015 | Shahriari | |
| 8,945,209 B2 | 2/2015 | Bonyuet et al. | |
| 8,961,595 B2 | 2/2015 | Alkhatib | |
| 8,974,523 B2 | 3/2015 | Thill et al. | |
| 8,974,524 B2 | 3/2015 | Yeung et al. | |
| 9,186,249 B2* | 11/2015 | Rolando | A61F 2/2418 |
| 2001/0010017 A1 | 7/2001 | Letac et al. | |
| 2001/0021872 A1* | 9/2001 | Bailey | A61F 2/2418 623/1.24 |
| 2002/0036220 A1 | 3/2002 | Gabbay | |
| 2002/0138138 A1* | 9/2002 | Yang | 623/2.18 |
| 2003/0023303 A1 | 1/2003 | Palmaz et al. | |
| 2003/0027332 A1 | 2/2003 | Lafrance et al. | |
| 2003/0036791 A1 | 2/2003 | Philipp et al. | |
| 2003/0050694 A1 | 3/2003 | Yang et al. | |
| 2003/0109924 A1* | 6/2003 | Cribier | 623/2.18 |
| 2003/0130726 A1 | 7/2003 | Thorpe et al. | |
| 2003/0199963 A1 | 10/2003 | Tower et al. | |
| 2003/0199971 A1 | 10/2003 | Tower et al. | |
| 2004/0039436 A1 | 2/2004 | Spenser et al. | |
| 2004/0049262 A1 | 3/2004 | Obermiller et al. | |
| 2004/0093075 A1 | 5/2004 | Kuehne | |
| 2004/0111111 A1 | 6/2004 | Lin | |
| 2004/0210304 A1 | 10/2004 | Seguin et al. | |
| 2004/0260389 A1 | 12/2004 | Case et al. | |
| 2005/0033398 A1 | 2/2005 | Seguin | |
| 2005/0096726 A1 | 5/2005 | Sequin et al. | |
| 2005/0113910 A1 | 5/2005 | Paniagua et al. | |
| 2005/0137682 A1 | 6/2005 | Justino | |
| 2005/0137686 A1 | 6/2005 | Salahieh et al. | |
| 2005/0137688 A1 | 6/2005 | Salahieh et al. | |
| 2005/0137689 A1 | 6/2005 | Salahieh et al. | |
| 2005/0137690 A1 | 6/2005 | Salahieh et al. | |
| 2005/0137691 A1 | 6/2005 | Salahieh et al. | |
| 2005/0137695 A1 | 6/2005 | Salahieh et al. | |
| 2005/0137696 A1 | 6/2005 | Salahieh et al. | |
| 2005/0137697 A1 | 6/2005 | Salahieh et al. | |
| 2005/0137698 A1 | 6/2005 | Salahieh et al. | |
| 2005/0137699 A1 | 6/2005 | Salahieh et al. | |
| 2005/0137701 A1 | 6/2005 | Salahieh et al. | |
| 2005/0143809 A1 | 6/2005 | Salahieh et al. | |
| 2005/0165477 A1 | 7/2005 | Anduiza et al. | |
| 2005/0177228 A1* | 8/2005 | Solem | A61F 2/2451 623/2.36 |
| 2005/0192665 A1 | 9/2005 | Spenser et al. | |
| 2005/0197695 A1 | 9/2005 | Stacchino et al. | |
| 2005/0203605 A1 | 9/2005 | Dolan | |
| 2005/0203616 A1 | 9/2005 | Cribier | |
| 2005/0251251 A1 | 11/2005 | Cribier | |
| 2005/0256566 A1 | 11/2005 | Gabbay | |
| 2006/0004439 A1 | 1/2006 | Spenser et al. | |
| 2006/0008497 A1 | 1/2006 | Gabbay | |
| 2006/0052867 A1 | 3/2006 | Revuelta et al. | |
| 2006/0058872 A1 | 3/2006 | Salahieh et al. | |
| 2006/0074484 A1* | 4/2006 | Huber | 623/2.11 |
| 2006/0122692 A1* | 6/2006 | Gilad et al. | 623/1.24 |
| 2006/0129235 A1 | 6/2006 | Seguin et al. | |
| 2006/0149360 A1 | 7/2006 | Schwammenthal et al. | |
| 2006/0161249 A1 | 7/2006 | Realyvasquez et al. | |
| 2006/0173532 A1 | 8/2006 | Flagle et al. | |
| 2006/0178731 A1 | 8/2006 | Tower | |
| 2006/0178740 A1* | 8/2006 | Stacchino et al. | 623/2.18 |
| 2006/0195183 A1* | 8/2006 | Navia et al. | 623/2.18 |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0253191 A1 | 11/2006 | Salahieh et al. | |
| 2006/0259120 A1 | 11/2006 | Vongphakdy et al. | |
| 2006/0259135 A1* | 11/2006 | Navia et al. | 623/2.11 |
| 2006/0259136 A1 | 11/2006 | Nguyen et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2006/0276874 A1 | 12/2006 | Wilson et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0050021 A1* | 3/2007 | Johnson | 623/2.14 |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0112355 A1 | 5/2007 | Salahieh et al. | |
| 2007/0112422 A1 | 5/2007 | Dehdashtian | |
| 2007/0118210 A1 | 5/2007 | Pinchuk | |
| 2007/0118214 A1 | 5/2007 | Salahieh et al. | |
| 2007/0142907 A1 | 6/2007 | Moaddeb et al. | |
| 2007/0162100 A1 | 7/2007 | Gabbay | |
| 2007/0162107 A1 | 7/2007 | Haug et al. | |
| 2007/0203503 A1 | 8/2007 | Salahieh et al. | |
| 2007/0208550 A1 | 9/2007 | Cao et al. | |
| 2007/0213813 A1 | 9/2007 | Von Segesser et al. | |
| 2007/0233228 A1 | 10/2007 | Eberhardt et al. | |
| 2007/0239271 A1 | 10/2007 | Nguyen | |
| 2007/0244545 A1 | 10/2007 | Birdsall et al. | |
| 2007/0244552 A1 | 10/2007 | Salahieh et al. | |
| 2007/0255398 A1* | 11/2007 | Yang et al. | 623/2.18 |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1* | 6/2008 | Nguyen | A61F 2/2412 623/2.11 |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0099653 A1 | 4/2009 | Suri et al. | |
| 2009/0112309 A1 | 4/2009 | Jaramillo et al. | |
| 2009/0138079 A1 | 5/2009 | Tuval et al. | |
| 2009/0171447 A1 | 7/2009 | Von Segesser et al. | |
| 2009/0248149 A1* | 10/2009 | Gabbay | 623/2.37 |
| 2009/0276027 A1 | 11/2009 | Glynn | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0168844 A1 | 7/2010 | Toomes et al. | |
| 2010/0185277 A1 | 7/2010 | Braido et al. | |
| 2010/0191326 A1 | 7/2010 | Alkhatib | |
| 2010/0204781 A1* | 8/2010 | Alkhatib | A61F 2/2418 623/1.26 |
| 2010/0204785 A1 | 8/2010 | Alkhatib | |
| 2010/0217382 A1 | 8/2010 | Chau et al. | |
| 2010/0234940 A1 | 9/2010 | Dolan | |
| 2010/0249911 A1 | 9/2010 | Alkhatib | |

(56) References Cited

U.S. PATENT DOCUMENTS

| | | | |
|---|---|---|---|
| 2010/0249923 A1 | 9/2010 | Alkhatib et al. | |
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2011/0054466 A1 | 3/2011 | Rothstein et al. | |
| 2011/0098800 A1* | 4/2011 | Braido | A61F 2/2412 |
| | | | 623/1.16 |
| 2011/0098802 A1 | 4/2011 | Braido et al. | |
| 2011/0137397 A1 | 6/2011 | Chau et al. | |
| 2011/0166636 A1* | 7/2011 | Rowe | A61F 2/2418 |
| | | | 623/1.11 |
| 2011/0172765 A1 | 7/2011 | Nguyen et al. | |
| 2011/0208283 A1 | 8/2011 | Rust | |
| 2011/0264206 A1 | 10/2011 | Tabor | |
| 2012/0035722 A1 | 2/2012 | Tuval | |
| 2012/0078347 A1 | 3/2012 | Braido et al. | |
| 2012/0101572 A1 | 4/2012 | Kovalsky et al. | |
| 2012/0123529 A1 | 5/2012 | Levi et al. | |
| 2012/0303116 A1 | 11/2012 | Gorman, III et al. | |
| 2013/0274873 A1* | 10/2013 | Delaloye | A61F 2/2409 |
| | | | 623/2.18 |
| 2014/0121763 A1 | 5/2014 | Duffy et al. | |
| 2014/0155997 A1 | 6/2014 | Braido | |
| 2014/0214159 A1 | 7/2014 | Vidlund et al. | |
| 2014/0228946 A1 | 8/2014 | Chau et al. | |
| 2014/0303719 A1 | 10/2014 | Cox et al. | |
| 2014/0324164 A1* | 10/2014 | Gross | A61F 2/2442 |
| | | | 623/2.37 |
| 2014/0343671 A1 | 11/2014 | Yohanan et al. | |
| 2014/0350668 A1 | 11/2014 | Delaloye et al. | |
| 2014/0350669 A1 | 11/2014 | Gillespie et al. | |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 1926455 A2 | 6/2008 |
| EP | 2537487 A1 | 12/2012 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006041505 A1 | 4/2006 |
| WO | 2006073626 A2 | 7/2006 |
| WO | 2007053243 A2 | 5/2007 |
| WO | 2007071436 A2 | 6/2007 |
| WO | 2007/081820 A1 | 7/2007 |
| WO | 2008070797 A2 | 6/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

Heart repairs without surgery. Minimally invasive procedures aim to correct valve leakage. PubMed ID 15586429, Heart Advisor, Sep. 2004.

Andersen, H. R. et al, Transluminal implantation of artificial heart valves, European Heart Journal (1992) 13, 704-708.

Andersen, Henning Rud, Transluminal Catheter Implanted Prosthetic Heart Valves, International Journal of Angiology 7:102-106 (1998).

Buellesfeld et al., Treatment of paravalvular leaks through inverventional techniques; Department of Cardiology, Ben University Hospital 2011.

Catheter-implanted prosthetic heart valves, Knudsen, L.L., et al., The International Journal of Artificial Organs, vol. 16, No. 5 1993, pp. 253-262.

De Cicco, Giuseppe, et al. "Aortic valve periprosthetic leakage: anatomic observations and surgical results." The Annals of thoracic surgery 79.5 (2005): 1480-1485.

Gössl, Mario, and Charanjit S. Rihal. "Percutaneous treatment of aortic and mitral valve paravalvular regurgitation." Current cardiology reports 15.8 (2013): 1-8.

Maribeth et al., Transcatheter Umbrella Closure of Valvular and Paravalvular Leaks, Hourihan et al., Journal of the American College of Cardiology, vol. 20, No. 6, pp. 1371-1377, (1992).

Muñoz, Daniel Rodríguez, Carla Lázaro Rivera, and José Luis Zamorano Gómez. "Guidance of treatment of perivalvular prosthetic leaks." Current cardiology reports 16.1 (2014): 1-6.

Quaden, René et al., "Percutaneous aortic valve replacement: resection before implantation," 836-840, European J. of Cardio-thoracic Surgery 27 (2005).

Rohde, I., Masch, J.-M., Theisen-Kunde, D., Marczynski-Bühlow, M., Bombien Quaden, R., Lutter, G. and Brinkmann, R. (2015), Resection of Calcified Aortic Heart Leaflets In Vitro by Q-Switched 2?µm Microsecond Laser Radiation. Journal of Cardiac Surgery, 30: 157-162. doi: 10.1111/jocs.12481.

Ruiz, Carlos, Overview of PRE-CE Mark Transcatheter Aortic Valve Technologies, Euro PCR (powerpoint—dated May 25, 2010).

Swiatkiewicz, Iwona, et al. "Percutaneous closure of mitral perivalvular leak." Kardiologia polska 67.7 (2009): 762.

Transluminal Aortic Valve Placement, Moazami, Nader, et al., ASAIO Journal, 1996; 42:M381-M385.

U.S. Appl. No. 29/375,243, filed Sep. 20, 2010.

U.S. Appl. No. 29/375,260, filed Sep. 20, 2010.

Zegdi, Rachid, MD, PhD et al., "Is It Reasonable to Treat All Calcified Stenotic Aortic Valves With a Valved Stent?" 579-584, J. of the American College of Cardiology, vol. 51, No. 5, Feb. 5, 2008.

* cited by examiner

COLLAPSIBLE-EXPANDABLE PROSTHETIC HEART VALVES WITH STRUCTURES FOR CLAMPING NATIVE TISSUE

BACKGROUND OF THE INVENTION

This invention relates to prosthetic heart valves, and more particularly to prosthetic heart valves that can be collapsed to a relatively small size for delivery into a patient and then re-expanded to full operating size at the final implant site in the patient.

At present there is considerable interest in prosthetic heart valves that can be collapsed to a relatively small circumferential (or annular perimeter) size for delivery into a patient (e.g., through tubular delivery apparatus like a catheter, a trocar, laparoscopic instrumentation, or the like). This is of interest because it can help to make replacement of a patient's defective heart valve less invasive for the patient. When the prosthetic valve reaches the desired implant site in the patient, the valve is re-expanded to a larger circumferential (or annular perimeter) size, which is the full operating size of the valve.

Because of the interest in prosthetic heart valves of the above general type, improvements to valves of this type are always being sought.

SUMMARY OF THE INVENTION

In accordance with certain possible aspects of the invention, a prosthetic heart valve may include an annular structure that is annularly continuous and that has an annular perimeter that is changeable in length between (1) a first relatively small length suitable for delivery of the valve into a patient with reduced invasiveness, and (2) a second relatively large length suitable for use of the annular structure to engage tissue of the patient adjacent to the patient's native valve annulus and thereby implant the valve in the patient. The valve further includes a flexible leaflet structure attached to the annular structure. The annular structure may comprise an annular array of diamond-shaped cells. Upstream apex portions of at least some of these cells may be resiliently biased to deflect radially outwardly from at least some other portions of the annular structure, and downstream apex portions of at least some of these cells may also be resiliently biased to deflect radially outwardly from at least some other portions of the annular structure. As a result, when the valve is in use in a patient, tissue of the patient adjacent to the patient's native heart valve annulus is clamped between the upstream and downstream apex portions, with the upstream apex portions engaging tissue upstream from the annulus, and with the downstream apex portions engaging tissue downstream from the annulus.

In accordance with certain other possible aspects of the invention, a prosthetic aortic heart valve may include an annular structure that is annularly continuous and that has an annular perimeter that is changeable in length between (1) a first relatively small length suitable for delivery of the valve into a patient with reduced invasiveness, and (2) a second relatively large length suitable for use of the annular structure to engage tissue of the patient adjacent to the patient's native aortic valve annulus and also downstream from ostia of the patient's coronary arteries to thereby implant the valve in the patient. The annular structure may include an annularly continuous annulus portion adapted for implanting adjacent the patient's native aortic valve annulus upstream from the ostia of the patient's coronary arteries, and an annularly continuous aortic portion adapted for implanting in the patient's aorta downstream from those ostia. The annulus portion and the aortic portion are preferably connected to one another only by a plurality of linking structures that are disposed to pass through at least a portion of the patient's valsalva sinus at locations that are spaced from the ostia of the patient's coronary arteries in a direction that extends annularly around the valsalva sinus. The valve further includes a leaflet structure that is attached to the annulus portion. The annulus portion includes first and second tissue clamping structures that are spaced from one another along an axis that passes longitudinally through the valve, each of the clamping structures being resiliently biased to extend radially outwardly from the leaflet structure, whereby, in use, tissue of the patient adjacent to the patient's native aortic valve annulus is clamped between the first and second clamping structures, with the first clamping structure engaging tissue upstream from the annulus, and with the second clamping structure engaging tissue downstream from the annulus.

In accordance with certain still other possible aspects of the invention, a prosthetic aortic heart valve includes an annular structure that is annularly continuous and that has an annular perimeter that is changeable in length between (1) a first relatively small length suitable for delivery of the valve into a patient with reduced invasiveness, and (2) a second relatively large length suitable for use of the annular structure to engage tissue of the patient adjacent to the patient's native aortic valve annulus and thereby implant the valve in the patient. The valve further includes a flexible leaflet structure attached to the annular structure. When a valve having these aspects of the invention is implanted in the patient, any non-leaflet part of the valve that is at the level of the patient's native coronary artery ostia is confined in a direction that is circumferential of the valve to areas that are adjacent to the patient's native aortic valve commissures or downstream projections of those commissures, each of said areas having an extent in the circumferential direction that is less than the distance in the circumferential direction between circumferentially adjacent ones of those areas. In addition, the annular structure includes first and second tissue clamping structures that are spaced from one another along an axis that passes longitudinally through the valve. Each of the clamping structures is resiliently biased to extend radially outwardly from the leaflet structure, whereby, in use, tissue of the patient adjacent to the patient's native aortic valve annulus is clamped between the first and second clamping structures, with the first clamping structure engaging tissue upstream from the annulus, and with the second clamping structure engaging tissue downstream from the annulus.

Further features of the invention, its nature and various advantages, will be more apparent from the accompanying drawings and the following detailed description.

BRIEF DESCRIPTION OF THE DRAWINGS

FIG. 4 shows the depicted apparatus in its collapsed/pre-expanded state, and as though cut along a vertical line and then laid out flat.

DETAILED DESCRIPTION

Figure 1:
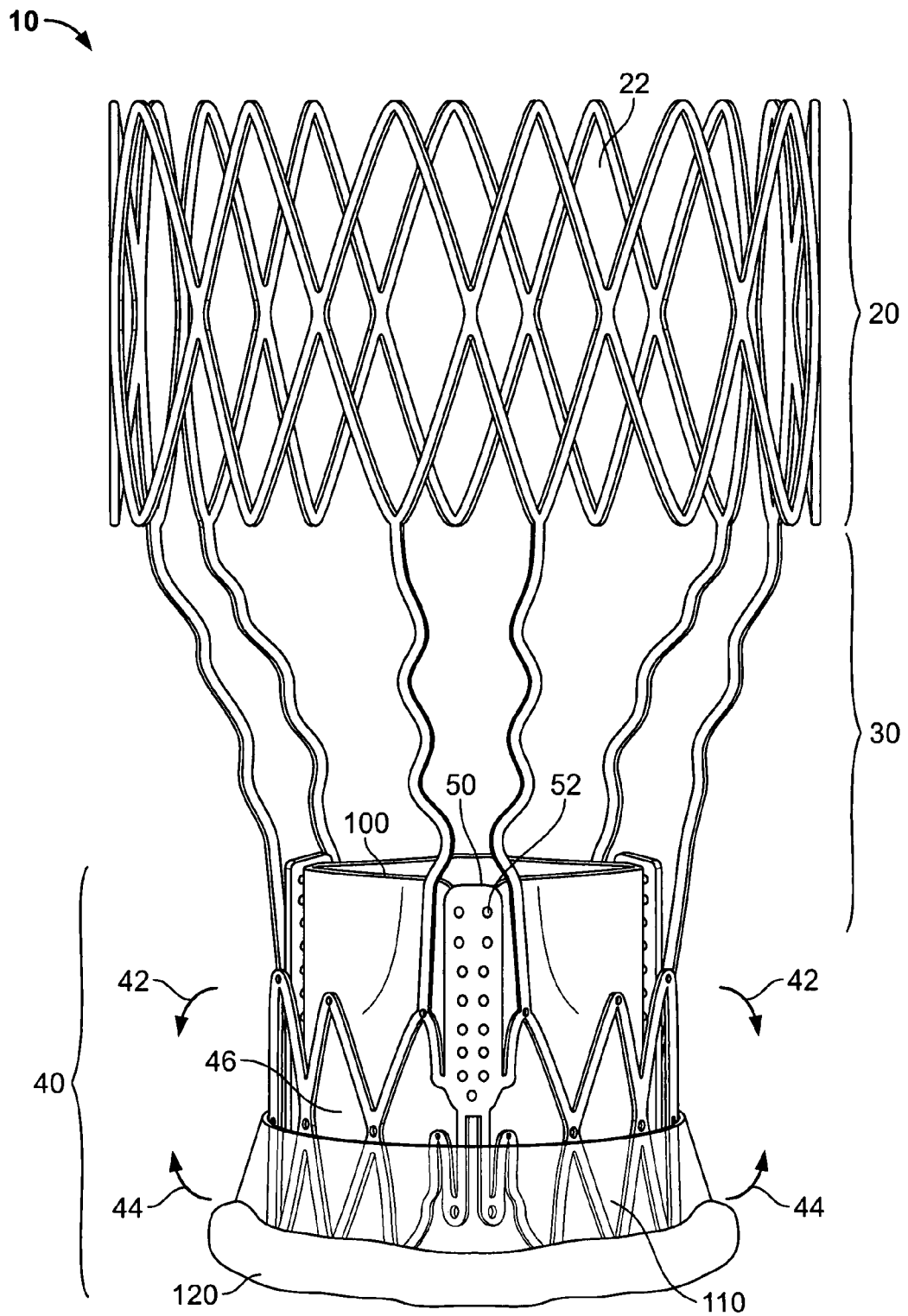
FIG. 1 is an elevational view of some components of an illustrative prosthetic valve in accordance with the invention.

Certain components of an illustrative embodiment of a prosthetic heart valve 10 in accordance with the invention are shown in FIG. 1. Valve 10 is designed for use as a replacement for a patient's native aortic valve. (Other valve types will be considered later in this specification.) FIG. 1 shows valve 10 in its expanded condition, i.e., the condition that the valve has when implanted in the patient. The depiction of valve 10 that is provided in FIG. 1 may omit certain components that the valve may have, but to some extent this is done to better reveal the components that are depicted in FIG. 1. More information will be provided about these possibly omitted components later in this specification. Also, FIG. 1 shows by representative arrows 42 and 44 that certain parts of the structure shown in the FIG. may deflect farther out and down (in the case of the parts associated with arrows 42) or farther out and up (in the case of the parts associated with arrows 44) than happens to be shown in FIG. 1. This will also be explained in more detail later in this specification.

Among the components of valve 10 are an annular metal structure 20/30/40, and a leaflet structure 100. Metal structure 20/30/40 forms a complete, continuous annulus around a longitudinal axis (not shown) that passes through the center of the valve. This central longitudinal axis is vertical, given the orientation of the valve shown in FIG. 1. Structure 20/30/40 can be reduced in annular size from the size shown in FIG. 1 by compressing that structure in the annular or circumferential direction. When this is done, structure 20/30/40 shrinks by partial collapse of the diamond-shaped cells 22 and 46 of aortic portion 20 and annulus portion 40. Later FIGS. will show examples of how such cells and/or other collapsible shapes can collapse or shrink in a direction that is annular of the valve. In other words, when the structure is thus made to shrink in the annular direction, the length of the perimeter measured around the outside of the valve becomes smaller. There is no significant change in the overall topological shape of the valve, especially metal structure 20/30/40, between its large and small perimeter sizes or at any time as it transitions between those sizes. For example, if the valve is approximately a circular annulus in its full (FIG. 1) size, it remains an approximately circular annulus as it is reduced to its smaller perimeter size. It is preferred that there be no folding, wrapping, overlapping, or other major topological shape change of metal structure 20/30/40 to reduce its perimeter size or to subsequently re-expand it.

The above-described changes (i.e., collapsing and re-expanding) of metal structure 20/30/40 are preferably all elastic deformations. For example, metal structure 20/30/40 can be resiliently biased to have the size and shape shown in FIG. 1. In such a case, collapsing of metal structure 20/30/40 to the above-mentioned smaller perimeter, annular, or circumferential size can be by elastic deformation of the metal structure, e.g., by confining metal structure 20/30/40 in a tube having a smaller perimeter than the full FIG. 1 size of the valve. Such a tube can be part of apparatus for delivering the valve into a patient. When the valve is pushed or pulled out of the tube, metal structure 20/30/40 automatically, elastically, re-expands to the full size shown in FIG. 1. Because such a delivery tube can be smaller than the full size of the valve, the valve can be delivered into the patient less invasively than would be possible if the valve was only capable of always remaining full size as shown in FIG. 1.

As an alternative or addition to full elastic compression and self-re-expansion, re-expansion may be at least partly assisted by other means. For example, an inflatable balloon on a catheter may be used to assist valve 10 to re-expand to its full size. Such a balloon may be temporarily positioned inside valve 10 to accomplish this. This may be done either because the elastic re-expansion is not quite strong enough to get the valve back to full size when adjacent to surrounding native tissue of the patient, because some plastic re-expansion is required to get the valve back to full size, to help ensure that the valve does in fact firmly seat in and engage the desired surrounding native tissue at the implant site, or for any other reason. For the most part it will be assumed herein that all or substantially all compression and re-expansion are elastic, but the possibility of some plastic compression and re-expansion is also contemplated as mentioned earlier in this paragraph.

We turn now to a description of the various parts of metal structure 20/30/40. Part 20 is intended for implantation in the patient's native aorta downstream from the native aortic valve location, and also downstream from the patient's native valsalva sinus. Part 20 may therefore be referred to as the aortic portion of the valve or of metal support structure 20/30/40. Portion 20 is a completely annular (continuous) structure, with the ability to annularly collapse and re-expand as described earlier in this specification. Portion 20 is made up principally of an annular array of parallelogram- or diamond-shaped cells 22, which give portion 20 the ability to annularly compress and re-expand as described.

Part 40 is intended for implantation in the patient's native aortic valve annulus. Part 40 may therefore be referred to as the annulus portion of the valve or of metal support structure 20/30/40. Part 40 is also a completely annular (continuous) structure, with the ability to annularly collapse and re-expand as described earlier in this specification. Part 40 is again made up primarily of an annular array of parallelogram- or diamond-shaped cells 46, which give portion 40 the ability to annularly compress and re-expand as described.

Part 40 also includes three commissure post members 50 that are spaced from one another (e.g., approximately equally) around the valve. Each commissure post member 50 is intended for implantation at the approximate angular or circumferential location of a respective one of the patient's native aortic valve commissures. Like the native commissures, posts 50 are structures at which adjacent ones of the three leaflets of structure 100 came together in pairs. The blood inflow edge portions (lower as viewed in FIG. 1) of each leaflet are also secured to other structure of the valve below posts 50. The blood outflow edge portions of leaflets 100 (upper as viewed in FIG. 1) are free (except for their end attachments to a respective pair of posts 50). These free edges can come together to close the valve when blood pressure downstream from the valve is greater than blood pressure upstream from the valve. When the blood pressure differential reverses, the greater upstream blood pressure pushes the free edges of the leaflets apart, thereby opening the valve to allow blood flow through it.

Leaflet structure 100 is typically made of three flexible leaflet sheets. The material of these sheets can be any known flexible leaflet material such as appropriately treated natural tissue, a flexible polymer, or the like.

Each of commissure posts 50 is preferably at least partly cantilevered up (in the blood flow direction) from remaining structure of part 40. For example, toward its blood inflow (lower) end, each of posts 50 may be attached to other structure of part 40 only near and/or below the middle of that part in the longitudinal (vertical) direction. At least the upper (blood outflow) end portion of each post 50 is therefore cantilevered from that post's lower-end-portion connections to other structure of part 40. The upper end portion of each post 50 is accordingly preferably a free end (i.e., without any metal connection to other adjacent metal structure of part 40). This has a number of advantages. One of these advantages is that it makes at least the upper portions of posts 50 at least somewhat independent of the other metal structure 20/30/40 of the device. This makes it possible for at least the upper portions of posts 50 to have properties like flexure characteristics, deflection characteristics, final location characteristics, etc., that can be optimized for the purposes that these post portions must serve, while other portions of metal structure 20/30/40 can be relatively independently optimized in these various respects for the various purposes that these other portions of structure 20/30/40 must serve. As an example of this, it may be desirable for the upper portions of posts 50 to stand relatively straight up and to have flexibility that is optimized for absorbing stress from the lateral edges of the leaflets 100 that are attached to those posts. At the same time, it may be desirable for other portions of metal structure 20/30/40 that are at the same general level along the longitudinal axis of the valve to flare radially out to various degrees. This will be described in more detail later in this specification. But just to complete the point that has been started here, it may be desired for the upper portions of cells 46 to be strong enough to hold back native leaflets and/or native leaflet remnants, and/or to deflect down onto the blood outflow surface of the native valve annulus (especially in cases in which the native leaflets have been wholly or largely removed). Similarly, it may be desirable for the members of strut structures 30 to begin to incline radially outwardly as they extend toward circumferentially larger aortic portion 20 and/or as they pass through the patient's native valsalva sinus, which is also circumferentially larger than the native valve annulus.

Clarification of a point of terminology may be appropriate here. When this specification speaks of a structure extending radially outwardly or the like, this does not necessarily mean that this structure is exactly perpendicular to a longitudinal axis extending in the blood flow direction through the valve. It may only mean that the structure has at least some component of alignment that is radial of the valve, i.e., that the structure (or a geometric projection of the structure) forms some angle with the above-mentioned longitudinal axis. In short, as a general matter, a "radially extending structure" or the like does not have to be fully or exactly radial of the above-mentioned longitudinal axis, but may instead have only some vector component that is radial of that axis.

Figure 28:
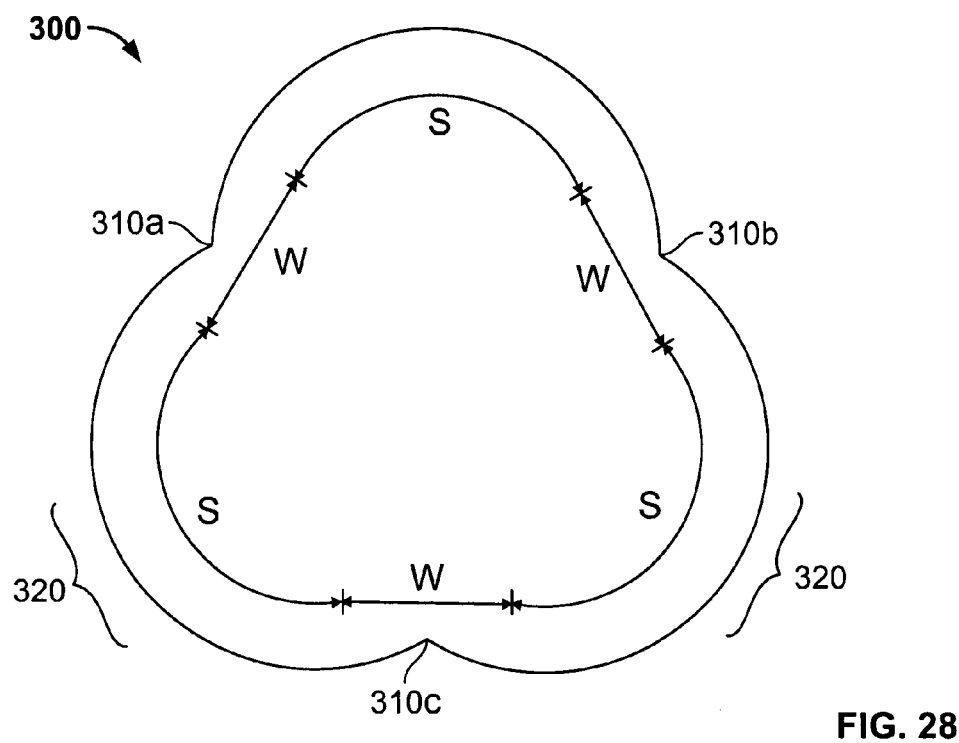
FIG. 28 is a simplified cross section of a typical patient tissue structure that is useful for explaining certain principles of the invention.

The aortic portion 20 and the annulus portion 40 of metal structure 20/30/40 are connected to one another by what may be termed struts or strut structures 30. In the illustrative embodiment shown in FIG. 1 there are six of these struts 30. They are in three pairs, with each pair being adjacent to a respective one of the three commissure posts 50. More particularly, the two struts 30 in each pair are preferably located adjacent (and relatively close to) respective opposite sides of the associated post 50. This arrangement leaves relatively large open areas (in the circumferential direction) between the pairs of struts 30. In other words, the distance in the circumferential direction between the struts 30 in any pair of those struts is preferably less than the circumferential distance between the two circumferentially closest struts in any two different pairs of those struts. Because commissure posts 50 are angularly or rotationally aligned with the patient's native aortic valve commissures, and because struts 30 pass through the patient's native valsalva sinus relatively close to longitudinal projections of posts 50, struts 30 are thus located to pass through the valsalva sinus (typically close to or at the wall of the valsalva sinus) along paths that are circumferentially spaced from the ostia of the patient's coronary arteries. In other words, struts 30 are preferably located in the circumferential direction to pass through the valsalva sinus without any possibility of a strut obstructing the ostium of a coronary artery. (Although patient anatomy can vary in this respect, the coronary artery ostia are typically located in the valsalva sinus between the native aortic valve commissures (or between longitudinal projections of the native aortic valve commissures). See also the later discussion of FIG. 28, which discussion applies to embodiments of the kind generally illustrated by FIG. 1. In particular, in the terms later discussed in connection with FIG. 28, all material of structure 30 at the level of the coronary artery ostia should be confined to areas W as shown in FIG. 28.)

In addition to the characteristics that are mentioned above, each of struts 30 is preferably serpentine in the longitudinal direction (i.e., as one proceeds along the length of any strut 30 from annulus portion 40 to aortic portion 20, the strut deviates from a straight line, first to one side of the straight line, then to the other side of the straight line, then back to the first side, and so on). One of the benefits of this type of strut configuration is that it can increase the lateral flexibility of structure 20/30/40, especially the lateral flexibility of strut portion 30 between portions 20 and 40. Lateral flexibility means flexibility transverse to a longitudinal axis that is parallel to blood flow through the valve. Prior to and during implantation, this lateral flexibility can help the valve more easily follow curves in instrumentation that is used to deliver the valve into the patient. After implantation, this lateral flexibility can help each of portions 20 and 40 seat more concentrically in its respective portion of the patient's anatomy, which portions may not be exactly perpendicularly concentric with one single, common, central longitudinal axis.

As shown in FIG. 1, the upper end of each strut 30 may connect to the lower end (or apex) of one of the cells 22 of aortic portion 20. The lower end of each struts 30 may similarly connect to the upper end (or apex) of one of the cells 46 of annulus portion 40. It should be noted, however, that especially at the lower end of strut structure 30 there are other cells 46 of annulus portion 40 that have no struts 30 connected to their upper ends or apexes. For example, arrows 42 are shown adjacent to the upper ends of two representative ones of cells 46 of this kind. These are the cells 46 whose upper portions can be configured to deflect or project radially outwardly (as indicated by the arrows 42) for such purposes (mentioned earlier, and also in more detail later) as holding back any remaining native leaflet material and/or clamping down on the blood outflow side of the patient's native valve annulus.

From the foregoing, it will be seen that the features of valve 10 for holding the valve in place in the patient can include any or all of the following: (1) the radially outward projection of some or all of the lower portions of annulus cells 46 adjacent the blood inflow side of the native aortic valve annulus; (2) the radially outward projection of the upper portions of at least some of the upper portions of annulus cells 46 adjacent possibly remaining native aortic leaflet tissue and/or adjacent the blood outflow side of the native aortic valve annulus; (3) the general radial outward expansion of annulus portion 40 against the native valve annulus; (4) the radial outward expansion of aortic portion 20 to annularly engage the inner wall surface of the aorta downstream from the valsalva sinus; and (5) the possible engagement of the inner wall surface of the valsalva sinus by strut structures 30 passing through that sinus. Although not shown in FIG. 1, it is possible to add to any suitable portion(s) of metal structure 20/30/40 barbs that project out from other adjacent structure so that they additionally engage, dig into, and/or penetrate tissue to give the implanted valve additional means for maintaining its position in the patient.

Note also that in addition to possibly engaging possibly remaining native aortic valve leaflet tissue, valve 10 has many structures for pushing any such remaining tissue radially outwardly away from possible interference with prosthetic leaflet structure 100. These structures include the upper portions of all of cells 46 and the lower portions of all of struts 30.

There are some other possible features of valve 10 that have not yet been mentioned. One of these aspects is the provision of apertures like 52 through commissure posts 50 (and possibly other portions of metal structure 20/30/40) for facilitating the attachment (e.g., using suture material or other similar strand material) of leaflet structure 100 to the metal structure. Other layers of material such as tissue, fabric, or the like may also be attached to various parts of metal structure 20/30/40 for various purposes. These purposes may include (1) helping to prevent, reduce, or cushion contact between leaflet structure 100 and metal structure 20/30/40; (2) helping to improve sealing between the valve and the surrounding native tissue (e.g., to prevent paravalvular leakage); and (3) helping to promote tissue in-growth into the implanted valve. Limited examples of such additional layers of material are shown in FIG. 1 in the form of lower fabric skirt 110 and blood inflow edge sealing ring 120. Both of structures 110 and 120 extend annularly around the outside of the lower (blood inflow) edge of valve 10. Structures like 110 and 120 may be held to metal structure 20/30/40 by sutures or other similar strand-like material, and apertures (like 52) through the metal structure (or other features of the metal structure) may be used to provide anchoring sites for such sutures or the like. Still other possible aspects of valve 10 will be discussed in connection with later FIGS.

A possibly important feature of valves in accordance with the present invention is that they can include a structure near the blood inflow edge for clamping adjacent native tissues in a particular way. In particular, the upper and lower portions of at least some of cells 46 can both pivot toward one another from a common central location. This is illustrated schematically in FIGS. 2 and 3.

Figure 2:
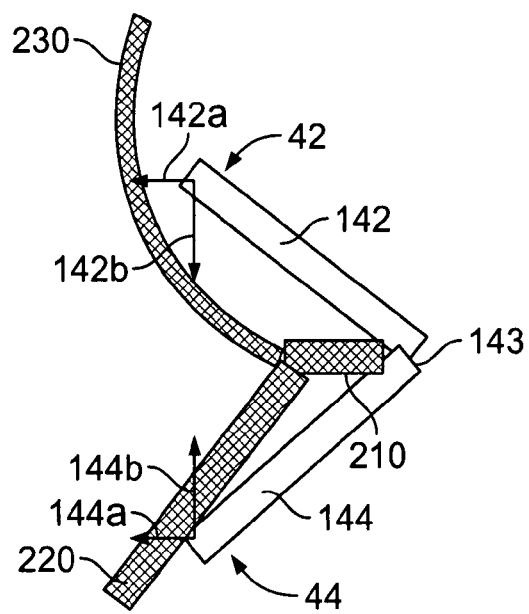
FIG. 2 is a simplified schematic diagram of a representative portion of apparatus like that shown in FIG. 1 in relation to some native tissue structures of a patient in accordance with the invention.

FIG. 2 shows the somewhat simpler case in which the patient's native aortic valve leaflets have been removed prior to implanting valve 10. The native tissue structures that are visible in FIG. 2 are a portion 220 of the wall of the left ventricle, a portion 210 of the aortic valve annulus, and a portion 230 of the wall of the valsalva sinus. The upper portion of a representative cell 46 from FIG. 1 is shown schematically in FIG. 2 by member 142. The lower portion of that cell is shown schematically by member 144. Members 142 and 144 can pivot toward one another about central pivot point 143. As in FIG. 1, this is again indicated by arcing arrows 42 and 44. Thus members 142 and 144 initially form a relative large, open jaw structure, the two jaws of which can be released to resiliently pivot toward one another to clamp down on any tissue within their reach. In the case of FIG. 2, this can include some of the tissue of sinus wall 230 and the upper surface of annulus 210 (for upper pivoting member 142), and some of the tissue of left ventricle wall 220 and the lower surface of annulus 210 (for lower pivoting jaw member 144). Clamping force vector component diagrams in FIG. 2 indicate the nature of the clamping forces that can result from these kinds of tissue engagement. For example, member 142 can have a radially outward clamping force component 142a and a longitudinally downward clamping force component 142b. Similarly, member 144 can have a radially outward clamping force component 144a and a longitudinally upward clamping force component 144b. Opposing clamping force components 142b and 144b tend to clamp tissue between members 142 and 144. But radially outward force components 142a and 142b also engage tissue and therefore also help to hold valve 10 in place in the patient.

Figure 3:
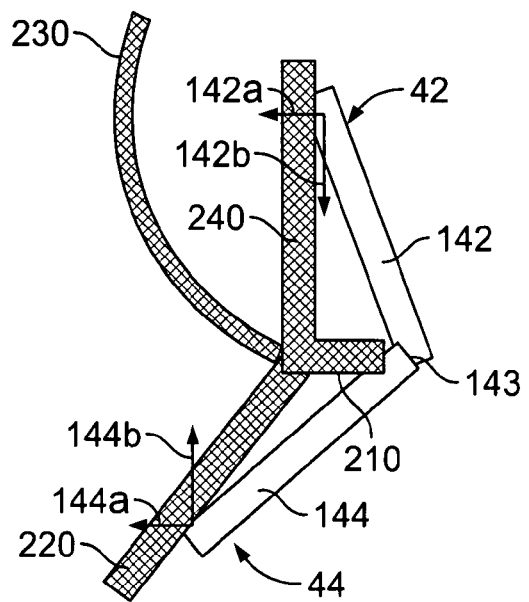
FIG. 3 is generally similar to FIG. 2 for some other native tissue structures of a patient.

FIG. 3 illustrates the somewhat more elaborate case in which native aortic leaflet tissue 240 (typically, or at least often, stenotic) remains in the vicinity of prosthetic valve 10 when the valve is implanted. FIG. 3 shows that in this type of situation upper member 142 both engages leaflet tissue 240 and helps to push it radially out of the way. Again, member 142 exerts both a radially outward force component 142a and a longitudinal (downward) force component 142b on the adjacent tissue (in this case leaflet tissue 240). The behavior and effects of lower member 144 are similar to what is shown in FIG. 2 and described earlier. Thus again the structures of valve 10 exert both radial outward tissue engaging forces 142a/144a and oppositely directed tissue clamping forces 142b/144b to hold valve 10 in place in the patient.

Recapitulating and extending the above, the attachment method of the present design applies forces in the radial and longitudinal directions to clamp onto several anatomical features, not just annulus 210. In doing this, a valve in accordance with this invention can maximize (or at least significantly increase) the orifice area at the annulus level for better blood flow. Another way of thinking about the present designs is not necessarily as "clamps," but rather as members of a stent 40 that conform to the different diameters of different portions of the anatomy. Structures that only "clamp" tend to engage only both sides of the native annulus (like 210), and do not also extend to and engage other tissue structures as in the present designs. The present structures also differ from "clamp" structures that terminate from a single pointed wire. Instead, in the present designs, the conforming members are formed from continuous strut members of the base (annular portion 40) of the stent. This can only be achieved with an annulus portion 40 that stays below the ostia of the coronary arteries and with commissure posts 50 that are "independent" of other structure of annulus portion 40 as was described earlier in this specification.

Still other features of the present valves that warrant emphasis are mentioned in the following. The annulus portion 40 of the present valves preferably expands as nearly as possible to the full size of the native valve annulus. The leaflet structure 100 is preferably mounted just inside annulus portion 40. This helps the present valves avoid any stenotic character (such as would result from having the leaflet structure or some other structure on which the leaflet structure is mounted) spaced radially inwardly from annulus portion 40. The present valves are thus ensured to have the largest opening for blood to flow through, which reduces the pressure gradient (drop) across the valve.

Note that at the level of the coronary artery ostia, the present valves have only very minimal non-leaflet structure 30; and even that minimal non-leaflet structure is rotationally positioned to pass through the valsalva sinus where it will safely bypass the coronary artery ostia. Annulus portion 40 is preferably designed to be entirely upstream (in the blood flow direction) from the coronary artery ostia. Aortic portion 20, on the other hand, is preferably designed to be entirely downstream from the coronary artery ostia (i.e., in the aorta downstream from the valsalva sinus). Some prior designs have much more extensive non-leaflet structures extending much farther into or through the valsalva sinus and therefore longitudinally beyond the coronary artery ostia. This is believed to be less desirable than the present structures.

The present valves preferably include "independent" commissure posts 50 that are "lined up" or aligned with (i.e., superimposed over) the native valve commissures. This also helps to ensure proper coronary artery flow, when combined with the fact that struts 30 are confined to being closely adjacent to posts 50 in the circumferential direction. Even relatively thin connecting members (like struts 30) could partially block a coronary artery if not correctly positioned in the circumferential direction around the valsalva sinus. But this is avoided in the present valves by the principles and features mentioned, for example, in the immediately preceding sentences.

Figure 4:
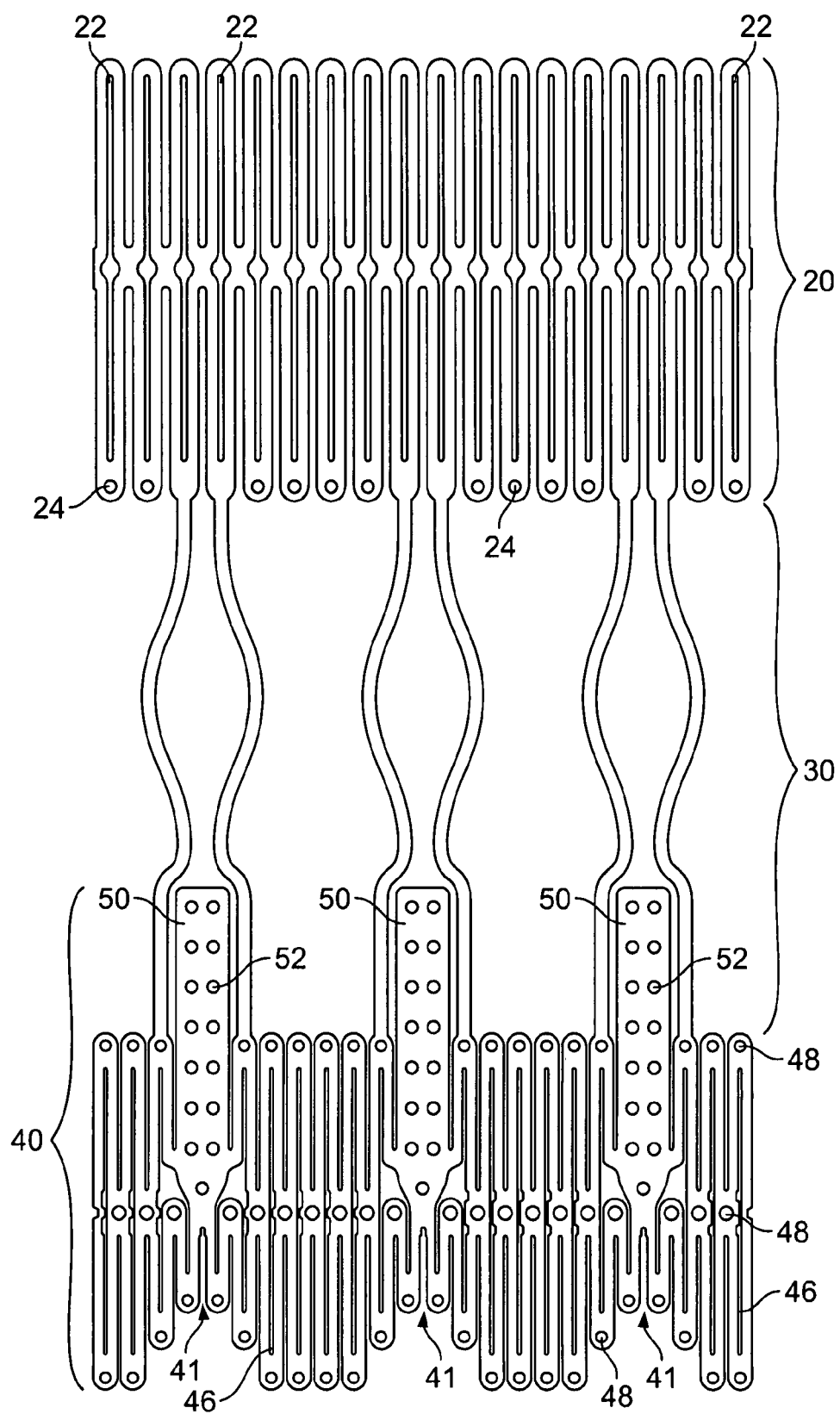
FIG. 4 is a simplified elevational view of another illustrative embodiment of apparatus in accordance with the invention.

FIG. 4 shows another illustrative embodiment of metal support structure 20/30/40. FIG. 4 shows this structure as though cut along its length and then laid flat. FIG. 4 also shows this structure in the condition that it has in its circumferentially collapsed condition. Thus, for example, the sides of what will be diamond-shaped cells 22 and 46 in the re-expanded valve are, in FIG. 4, collapsed down to being parallel with one another. Again, the fact that FIGS. like FIG. 4 show structures as though cut longitudinally and laid flat is only for ease and convenience of depiction. In actual fact these structures are complete and continuous annular structures like the structure 20/30/40 shown in FIG. 1.

Note that in the FIG. 4 design there are eyelets 24 in aortic section 20 for attachment of material and/or attachment of wires/sutures for a delivery system. On annulus section 40 the eyelets 48/52 can be used for attachment of the cuff, porcine buffer, and/or leaflets. FIG. 4 shows an annulus portion 40 with a "scalloped" inflow (lower) edge. This scalloped blood inflow edge is relatively "high" in the vicinity of the inflow end of each commissure post 50, and relatively "low" between commissure post 50 inflow ends. ("High" means more downstream; "low" means more upstream.) This can help the implanted valve avoid affecting the patient's mitral valve, which tends to be radially spaced from the aortic valve along a radius of the aortic valve that corresponds to the radial location of one of the aortic valve's commissures. Because the valves of this invention are preferably implanted with posts 50 superimposed inside the native valve commissures, this places one of the "high" portions 41 of the inflow edge adjacent the patient's mitral valve. The resulting recessing 41 of annulus portion 40 helps the prosthetic valve avoid interfering with the mitral valve.

Figure 5:
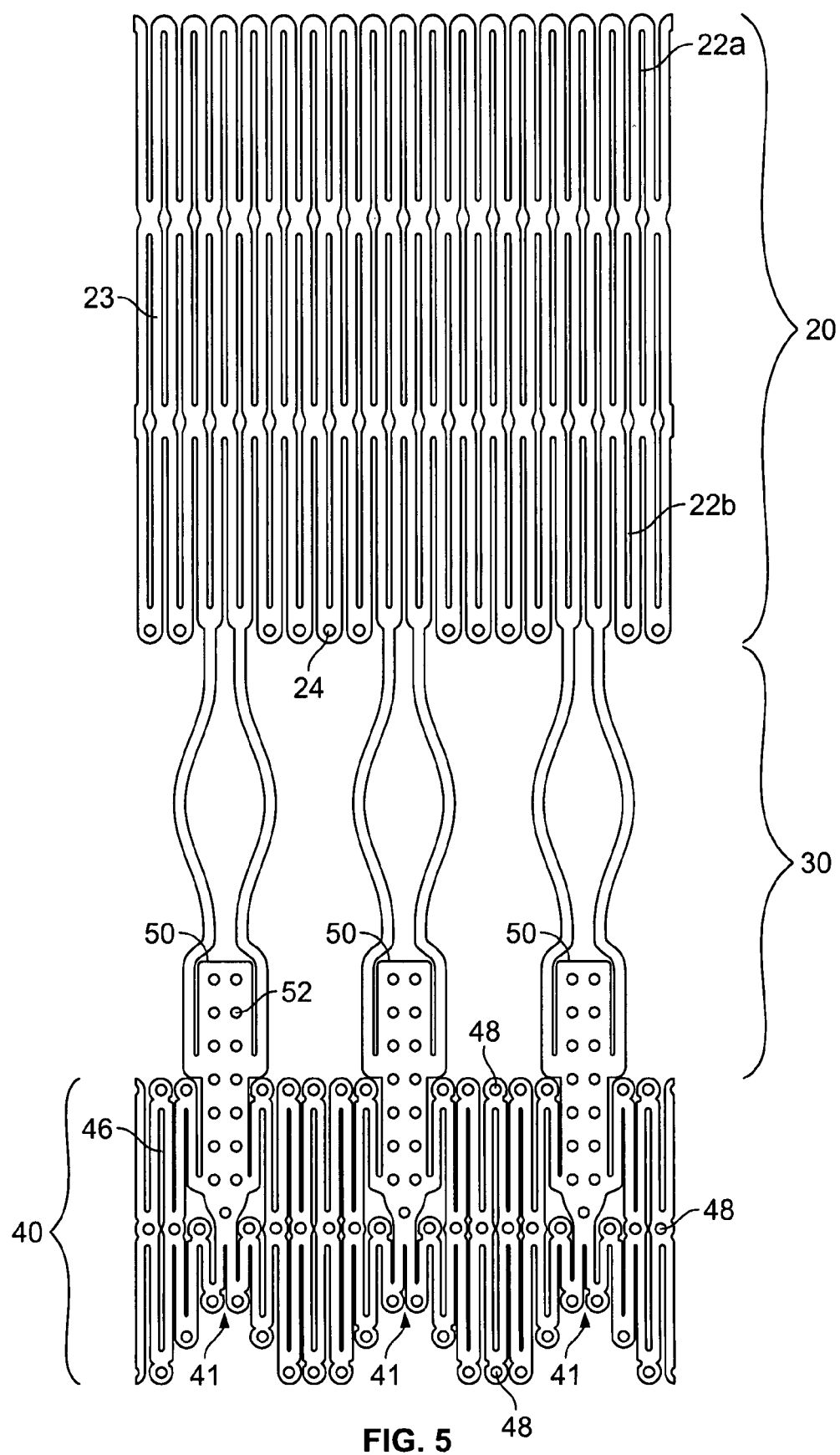
FIG. 5 is generally similar to FIG. 4 for another illustrative embodiment in accordance with the invention.

FIG. 5 shows yet another illustrative embodiment of metal support structure 20/30/40. FIG. 5 shows this embodiment in the same general way and condition as FIG. 4 shows its embodiment. Thus, as said in connection with FIG. 4, the structure shown in FIG. 5 is actually a complete, continuous annulus, and the longitudinally cut and flattened depiction shown in FIG. 5 is only employed for simplicity and greater clarity.

The FIG. 5 embodiment again has eyelets 24 in the aortic section 20 for attachment of material and/or attachment of wires/sutures for a delivery system. Also, eyelets 48/52 on annulus section 40 can be used for attachment of the cuff, porcine buffer, and/or leaflets. As compared to the FIG. 4 design (in which connecting support struts 30 are connected to the downstream apexes of certain annulus portion cells 46), in FIG. 5 the connecting support struts 30 are connected directly to posts 50. The aortic portion 20 of the FIG. 5 embodiment also has two annular arrays of cells 22a and 22b (rather than only one annular array of such cells 22 as in the earlier embodiments). Array 22a is more downstream than array 22b, but these two arrays do overlap somewhat in the longitudinal direction by virtue of the cells in the two arrays having some intervening cell members (like representative member 23) in common.

A typical way of making any of the support structures 20/30/40 of this invention is to laser-cut them from a tube.

Figure 6:
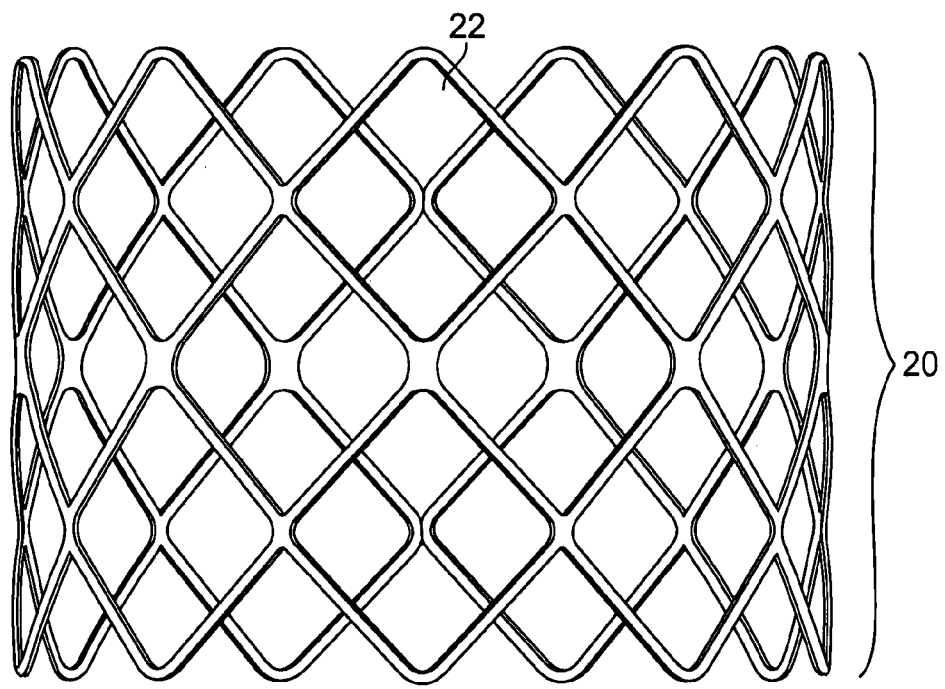
FIG. 6 is a simplified elevational view of another illustrative embodiment of apparatus in accordance with the invention.

FIG. 6 shows another illustrative embodiment of aortic portion 20, in which the cells 22 of the mesh stent can expand against the ascending aorta. This structure may or may not be covered in tissue, polymer, and/or fabric (true for any of the embodiments shown and described herein).

Figure 7:
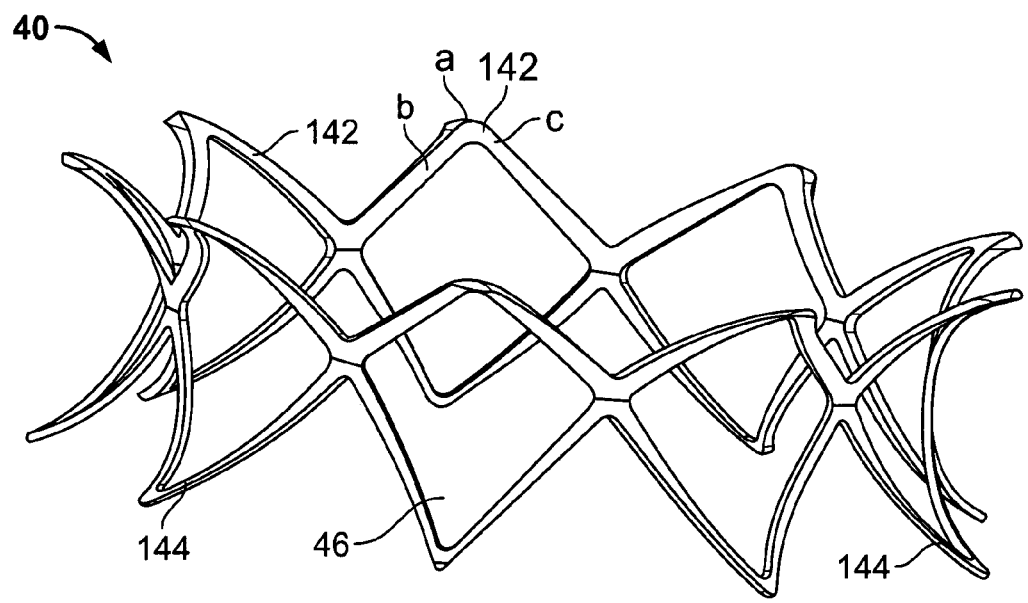
FIG. 7 is a simplified perspective view of another illustrative embodiment of apparatus in accordance with the invention.
Figure 8:
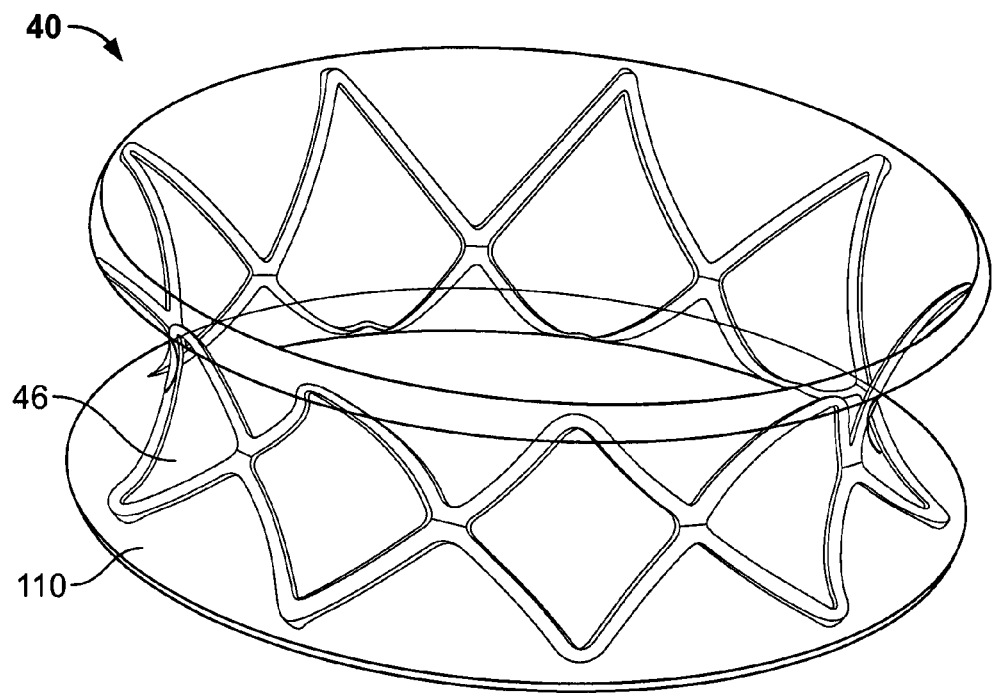
FIG. 8 is a simplified perspective view showing an illustrative embodiment of another component added to what is shown in FIG. 7 in accordance with the invention.

FIGS. 7 and 8 show another illustrative embodiment of annulus portion 40. This mesh stent has expandable cells that press against the native valve annulus and/or leaflets (if the native leaflets remain). Upper 142 and lower 144 portions of this stent clamp down on the native annulus and/or leaflets. This stent design is symmetrical around the circumference, but it may be asymmetrical to allow anatomical conformance with the mitral valve, for example. A cuff 110 made of fabric, tissue, or polymer may fully or partially encapsulate this stent as shown, for example in FIG. 8.

Figure 9:
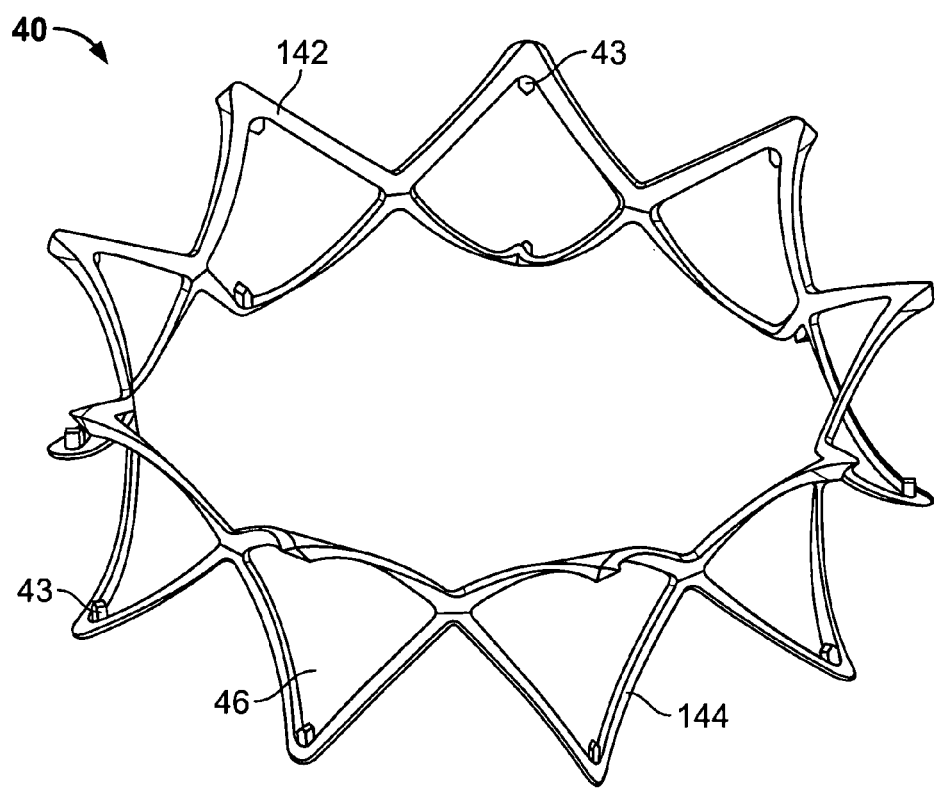
FIG. 9 is generally similar to FIG. 8, but shows an alternative embodiment with additional possible features in accordance with the invention.
Figure 10:
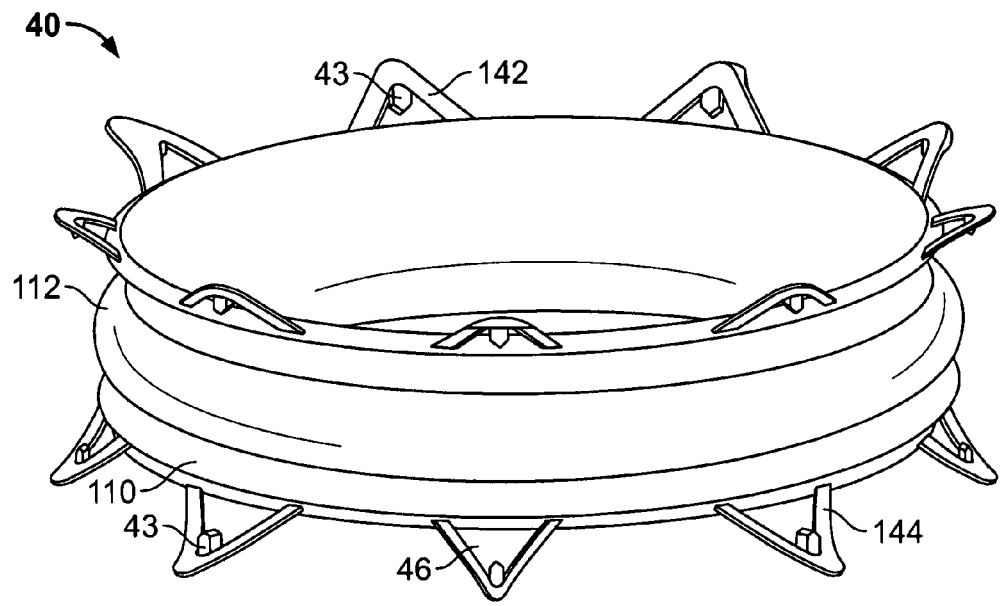
FIG. 10 is generally similar to FIG. 9, but shows an illustrative embodiment of more components added to what is shown in FIG. 9 in accordance with the invention.

FIGS. 9 and 10 show an embodiment of stent 40 that includes a set of barbs 43 on the top and/or bottom to further secure the stent in order to stop migration. A partial cuff 110 (FIG. 10) allows the barbed tips 43 to be exposed to direct tissue contact for enhanced securing. The bottom section could be asymmetrical (e.g., as in FIGS. 4 and 5) to mitigate any impingement on the mitral valve. An extra-thick, toroidal section 112 of the cuff allows extra sealing capacity to prevent paravalvular leakage.

Figure 11:
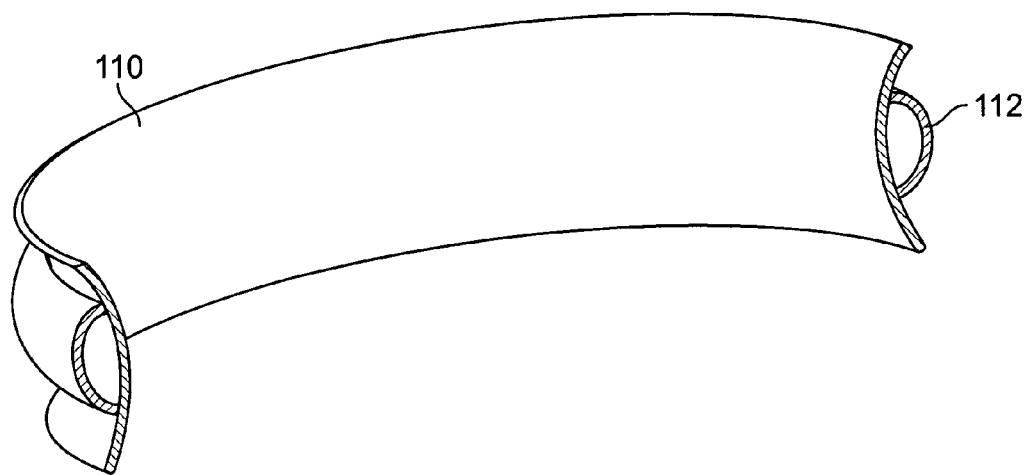
FIG. 11 is a simplified perspective view showing in more detail a representative portion of the components that are added in FIG. 10.

FIG. 11 shows that toroidal section 112 of cuff 110 allows extra sealing capacity to prevent paravalvular leakage. This section could be made of extra fabric, tissue, or polymer. The chamber 114 inside section 112 can accommodate an injectable polymeric substance to aid in seating.

Figure 12:
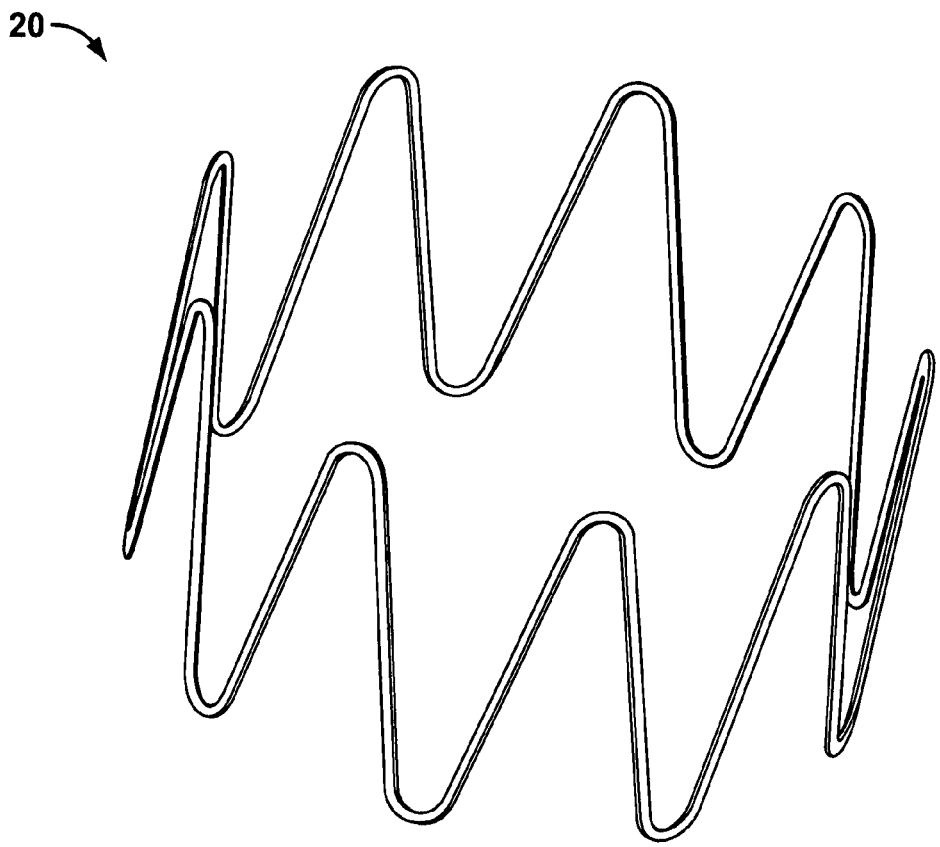
FIG. 12 is a simplified perspective view of another illustrative embodiment of apparatus in accordance with the invention.

FIG. 12 shows another illustrative embodiment of the aortic holding portion 20. In this case portion 20 is a metallic or polymeric expandable wire form with many of the same attributes discussed with the mesh stent.

Figure 13:
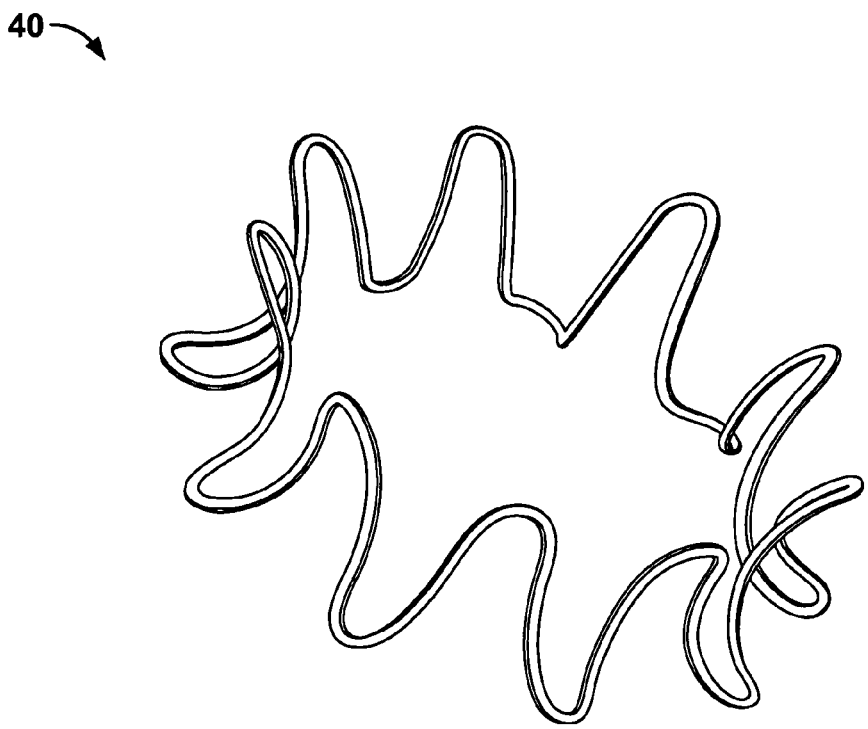
FIG. 13 is a simplified perspective view of another illustrative embodiment of apparatus in accordance with the invention.

FIG. 13 shows another illustrative embodiment of annulus/leaflet holding portion 40. In this case portion 40 is a metallic or polymeric expandable wire form with many of the same attributes discussed with the mesh stent.

Figure 14:
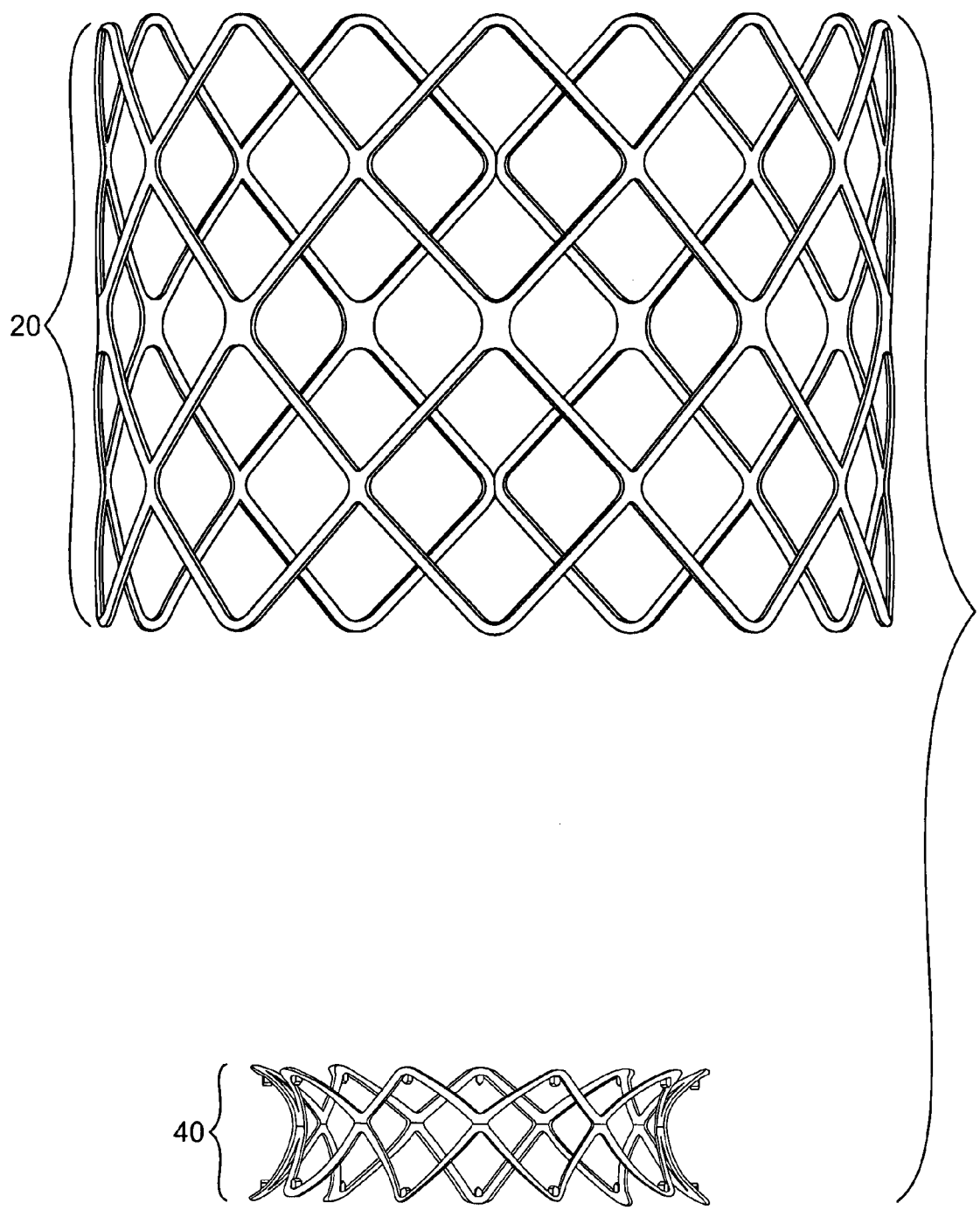
FIG. 14 is a simplified elevational view of still another illustrative embodiment of apparatus in accordance with the invention.
Figure 15:
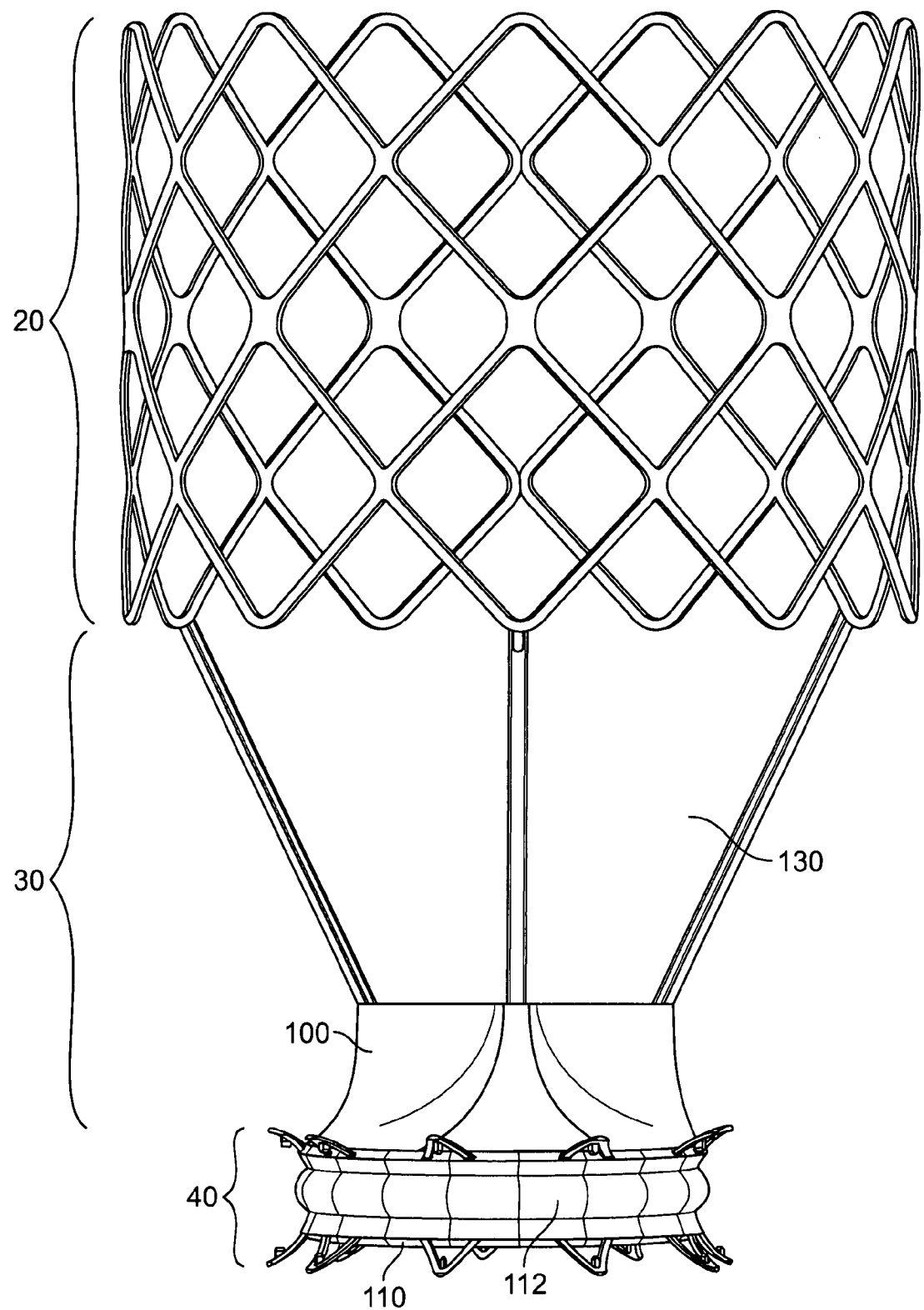
FIG. 15 is generally similar to FIG. 14, but shows an illustrative embodiment of more components added to what is shown in FIG. 14 in accordance with the invention.

FIGS. 14 and 15 show an illustrative assembly of an aortic portion 20 and an annulus portion 40. In FIG. 15 a pliable or semi-rigid reinforced fabric 30 connects the aortic portion 20 and the annulus/cuff portion 40/110/112 to allow somewhat independent movement. The tissue or synthetic leaflets 100 can then be attached to connecting section 30. All of the disclosed variations allow for ample areas (like 130) for blood to flow to the coronaries.

Figure 16:
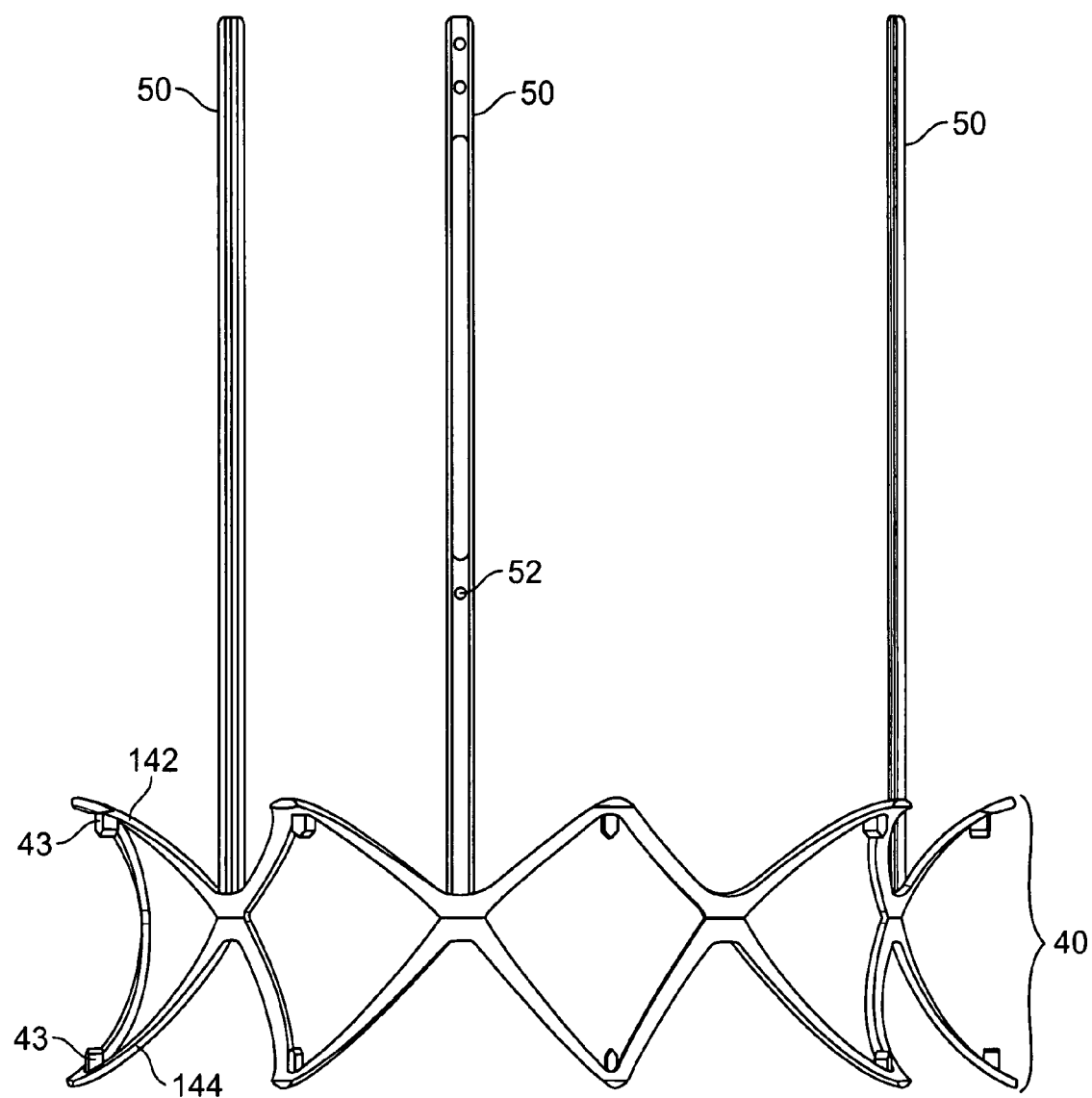
FIG. 16 is a simplified elevational view of another illustrative embodiment of apparatus in accordance with the invention.

The variation shown in FIG. 16 does not include an aortic portion 20. Instead, three independent commissure posts 50 allow for leaflet attachment (e.g., with the aid of apertures 52), while the base 40 is secured in place as described earlier. Posts 50 can be lined up with the native commissures and (by virtue of the recesses like the one identified by reference number 41) allow for an opening on the lower portion to be clear of chordae and the mitral valve. The posts 50 used to attach the leaflets may be solid or have any combination of holes, slots, and/or other apertures 52.

Note that even for an embodiment like FIG. 16, when used for an aortic valve, any non-leaflet portion of the valve (such as commissure posts 50) that extends into the coronary sinus to the level of any coronary artery ostium is confined, in the circumferential direction, to locations that are well spaced from the coronary artery ostia. This is preferably accomplished by having all such non-leaflet structure confined (in the circumferential direction) to locations or areas that are at or circumferentially near the native aortic valve commissures (or downstream projections of those commissures). The circumferential width of each of these areas in which non-leaflet structure is permitted at the level of the coronary artery ostia is preferably less than the circumferential spacing at that level between circumferentially adjacent ones of those areas. It is not a problem for moving leaflet material to extend to or even beyond the level of the coronary artery ostia because the coronary arteries can fill with blood when the valve is closed. But no non-leaflet and therefore basically non-moving part of the prosthetic valve should be allowed to occupy any location at the level of the coronary artery ostia where that non-leaflet material may interfere with blood flow into the coronary arteries.

FIG. 28 illustrates the point made in the immediately preceding paragraph (and also elsewhere in this specification). FIG. 28 shows a cross section of a typical patient's valsalva sinus 300 at the level of the coronary artery ostia. The patient's native aortic commissures (or downstream projections of those commissures) are at locations 310a-c. The coronary artery ostia typically occur in bracketed areas 320. Any non-leaflet structure of a prosthetic valve in accordance with this invention that is at the level depicted by FIG. 28 should be confined to areas W. The width of each of these areas in the circumferential direction (i.e., the dimension W) is preferably less than the distance S in the circumferential direction between any two circumferentially adjacent ones of these areas.

Figure 17:
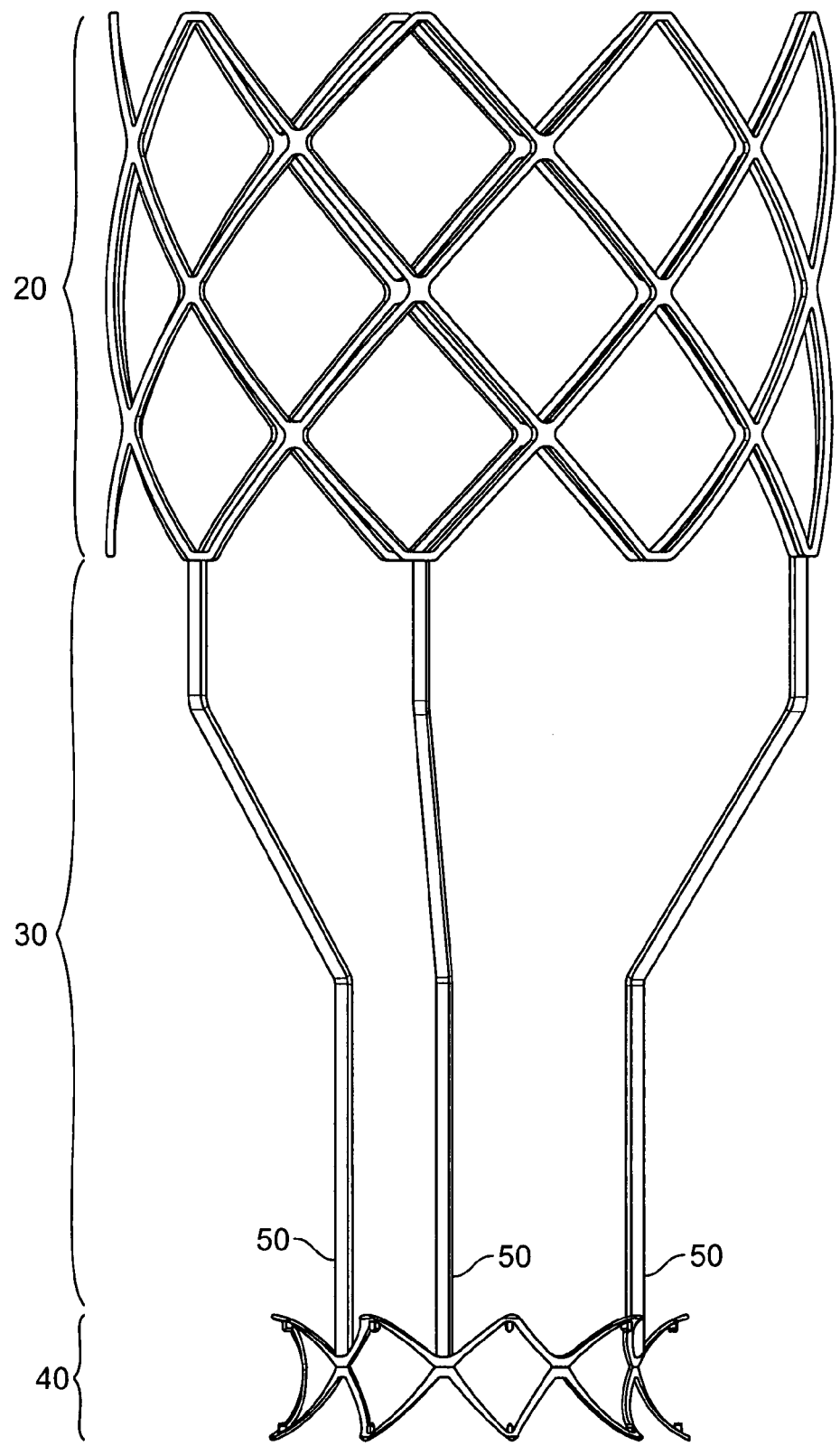
FIG. 17 is a simplified elevational view of another illustrative embodiment of apparatus in accordance with the invention.

FIG. 17 shows another illustrative embodiment that is somewhat like the embodiments in FIGS. 1, 4, and 5 in that there is a continuous link 30 between aortic section 20 and annulus section 40. In this embodiment link structure 30 itself allows for leaflet attachment, with the lower portion of each link 30 acting like a commissure post 50. To mitigate leaflet abrasion at the attachment site in this or any other embodiment, the stent may first be covered with fabric, followed by a thin layer of buffering tissue/polymer, and finally the leaflet tissue/polymer. The stent of the valve can be partially or completely covered in one or a combination of materials (polyester, tissue, etc.) to allow for better in-growth, abrasion protection, sealing, and protection from metal leachables like nickel from nitinol.

Most of the detailed discussion thus far in this specification has related to prosthetic aortic valves. However, certain aspects of what has already been said can also be applied to making prosthetic valves for other locations in the heart. The mitral valve is another valve that frequently needs replacement, and so this discussion will now turn to possible constructions for other valves such as the mitral valve.

In the case of the mitral valve (which supplies blood from the left atrium to the left ventricle), only the native valve annulus area (possibly including what is left of the native valve leaflets) is available for anchoring the prosthetic valve in place. There is nothing comparable to the aorta for additional downstream anchoring of a prosthetic mitral valve.

Structures of the types shown in FIGS. 7-11 and 13 are suitable for use in prosthetic mitral valves. In such use, annular structure 40 may be delivered into the native mitral valve annulus in a circumferentially collapsed condition and then re-expanded to the depicted size and condition in that annulus. The apex portions 142 of cells 46 at one end of structure 40 (e.g., the blood inflow end) project resiliently out and also pivot somewhat downstream as shown, for example, in FIG. 7 and engage the patient's tissue adjacent the inflow side of the patient's native mitral valve annulus. Apex portions 144 of cells 46 at the other end of structure 40 (e.g., the blood outflow end) project resiliently out and also pivot somewhat upstream and engage the patient's tissue adjacent the outflow side of the patient's native valve annulus. The tissue of and adjacent to the mitral valve annulus is thereby clamped between tissue clamping structures 142 and 144. Barbs 43 may be added as shown in FIGS. 9 and 10 for additional tissue engagement and possible penetration to additionally help hold the valve in place in the mitral valve annulus. Other features (e.g., 110 and 120) and principles discussed earlier in connection with FIGS. 7-11 and 13 apply to the possible mitral valve use of these structures and features.

Figure 18:
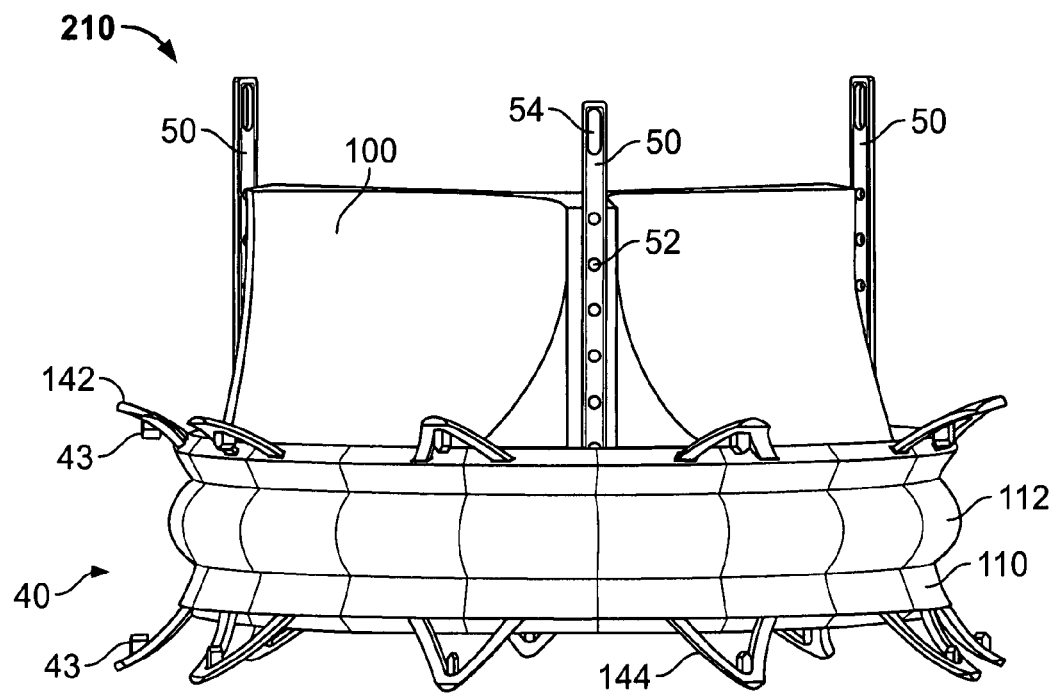
FIG. 18 is a simplified elevational view of another illustrative embodiment of a prosthetic heart valve in accordance with the invention.

An illustrative embodiment of a more fully developed prosthetic mitral valve 210 in accordance with the invention is shown in FIG. 18. In this depiction of mitral valve 210, its blood inflow end is down, and its blood outflow end is up. (This depiction may be regarded as "upside down" as compared to its orientation in a patient who is standing upright.) Analogous to what is shown in FIG. 16, valve 210 has three commissure posts 50 that are cantilevered from annular structure 40. Flexible valve leaflets 100 are attached to these posts (and elsewhere to other structure of the valve such as annular structure 40 and/or material that is used to cover structure 40). Apertures 52 through posts 50 may be used to facilitate attachment (e.g., suturing) of the leaflets to the posts. Additional apertures 54 in posts 50 may be used as sites for or to facilitate attachment of chordae tendonae (native and/or artificial replacements) to the posts. This last point will be considered further as the discussion proceeds.

The posts 50 used to attach the leaflets can be solid or can have any combination of holes and/or slots. Three independent posts 50 (i.e., "independent" because cantilevered from annular structure 40) allow for leaflet attachment, while the base 40 is secured in place as described earlier. Also, posts 50 can be lined up with the native anatomy for better leaflet opening clear of chordae and the aortic valve. Apertures 54 can be included near the downstream free ends of posts 50 for native and/or artificial chordae attachment. To mitigate leaflet abrasion at the attachment site, the stent 40 can first be covered with fabric, followed by a thin layer of buffering tissue/polymer, and finally the leaflet 100 tissue/polymer. As is true for all embodiments herein, the stent 40 of the valve can be partially or completely covered in one or a combination of materials (polyester, tissue, etc.) to allow for better in-growth, abrasion protection, sealing, and protection from metal leachables such as nickel from nitinol. The support structure 50 for the leaflets may be continuous from the clamping stent portion 40. Alternatively, the leaflet support structure may be a separate section connected to clamping portion 40, or it may be frameless.

Figure 19:
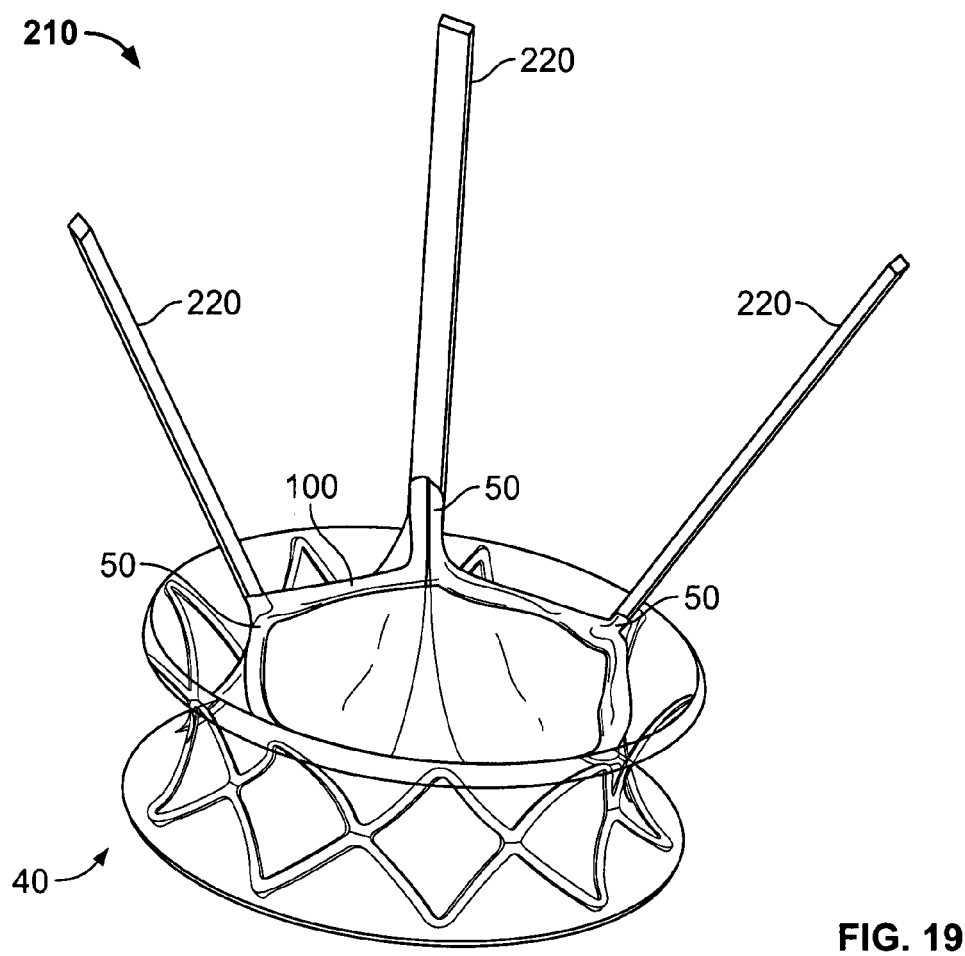
FIG. 19 is a simplified perspective view of an embodiment like that shown in FIG. 18 with other possible elements added in accordance with the invention.

FIG. 19 shows an example of how artificial and/or native chordae 220 can be attached prior to, during, or after implanting prosthetic mitral valve 210. These chordae attachments are made at or near the downstream free ends of posts 50. Chordae 220 can be adjusted through cored papillary muscles and/or through a port made in the apex of the beating heart.

Figure 20:
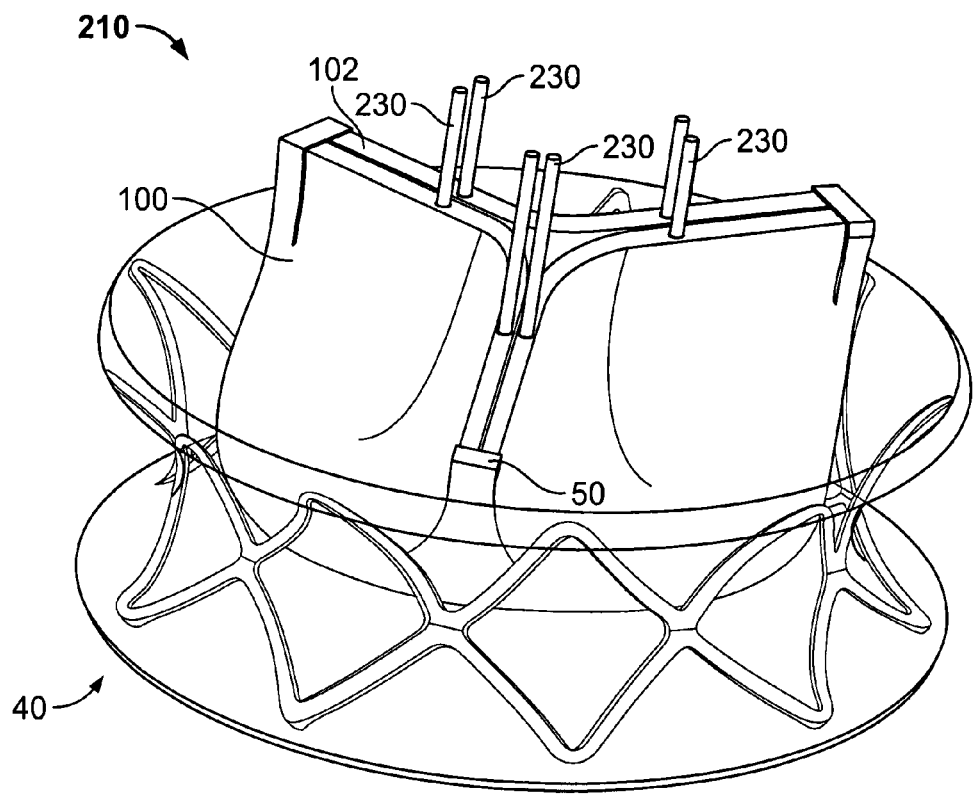
FIG. 20 is a simplified elevational view of another illustrative of a prosthetic heart valve in accordance with the invention.

FIG. 20 shows an alternative embodiment of prosthetic mitral valve 210 in which chordae 230 can be attached to an extended free edge 102 of the leaflets prior to, during, or after implanting of the valve in the patient. Once again, chordae 230 can be adjusted through cored papillary muscles and/or through a port made in the apex of the beating heart. The redundant coaptation portions 102 of the leaflets can be reinforced tissue (e.g., a double layer or thicker tissue), or if the leaflet is a polymer, it can be reinforced by greater thickness and/or fibers.

Figure 21:
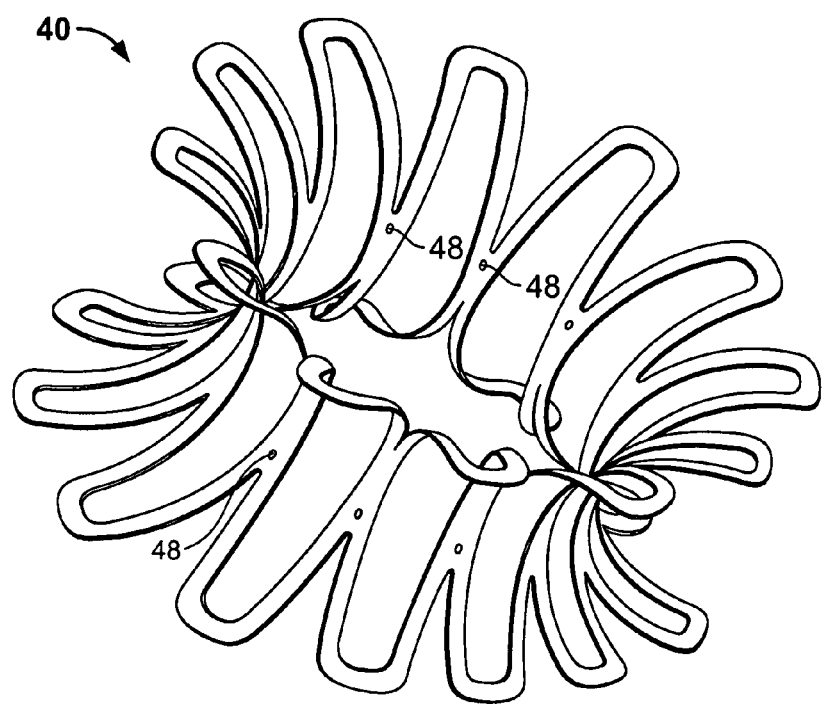
FIG. 21 is a simplified perspective view of another illustrative embodiment of a component for a prosthetic heart valve in accordance with the invention.
Figure 22:
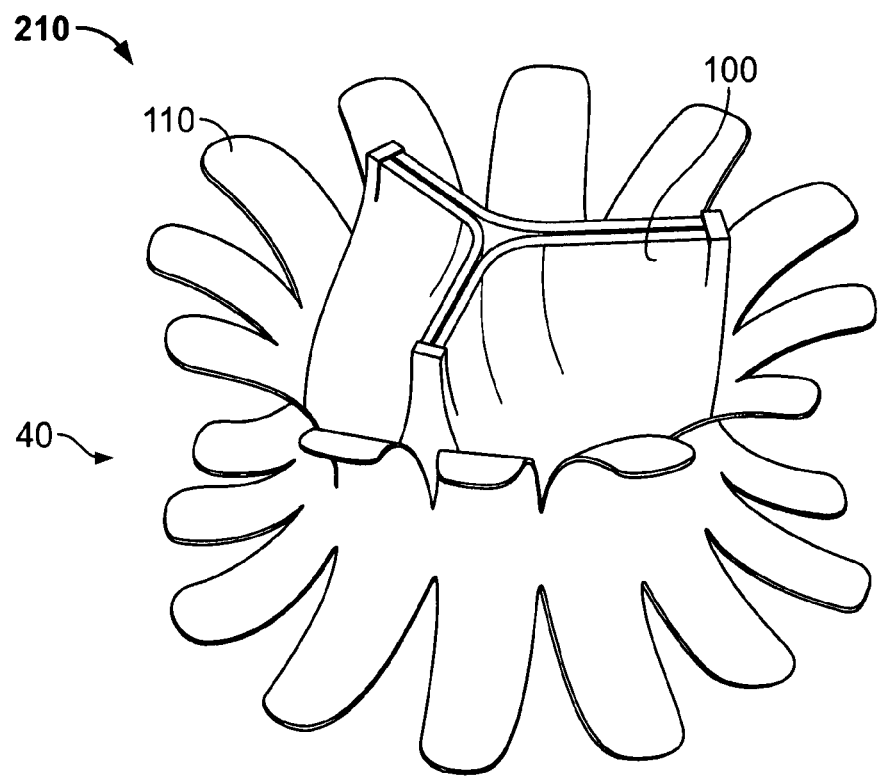
FIG. 22 is a simplified perspective view of another illustrative embodiment of a prosthetic heart valve in accordance with the invention.
Figure 23:
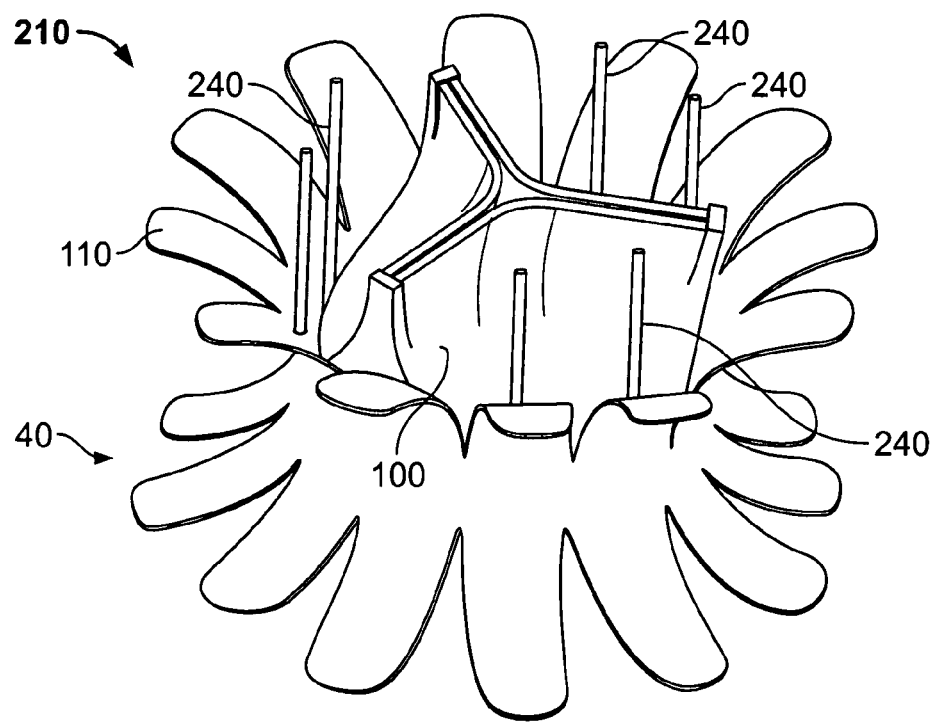
FIG. 23 is a simplified perspective view of another illustrative embodiment of a prosthetic heart valve in accordance with the invention.

FIG. 21 shows that the stent 40 design can include apertures 48 around the center portion of the stent to allow for cuff, leaflet, and chordae attachment around the circumference of the stent. FIG. 22 shows that the edge of cuff 110 can follow the edge shape of stent 40 to allow for passage of chordae and reduction of interference of other anatomy, while also allowing greater flexibility of annular structure 40. FIG. 23 shows chordae 240 extending from apertures like those shown at 48 in FIG. 21.

Figure 24:
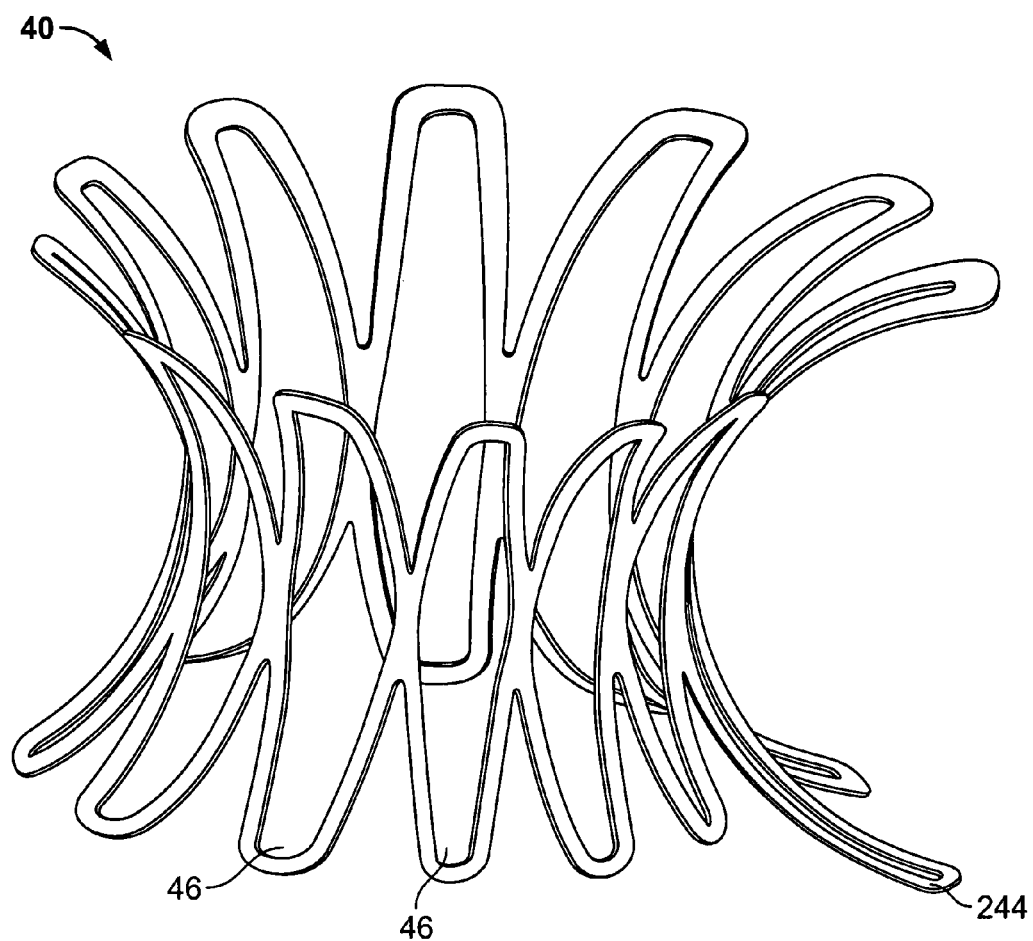
FIG. 24 is a simplified perspective view of another illustrative embodiment of a component for a prosthetic heart valve in accordance with the invention.

FIG. 24 illustrates the point that variations in stent cell 46 geometry around the circumference of annular structure 40 can reduce impingement on or of the aortic valve, chordae, and the coronary sinus. Additionally, extended portions (e.g., 244) of some cells may allow for greater holding force in certain parts of the anatomy such as in the atrial appendage.

Figure 25:
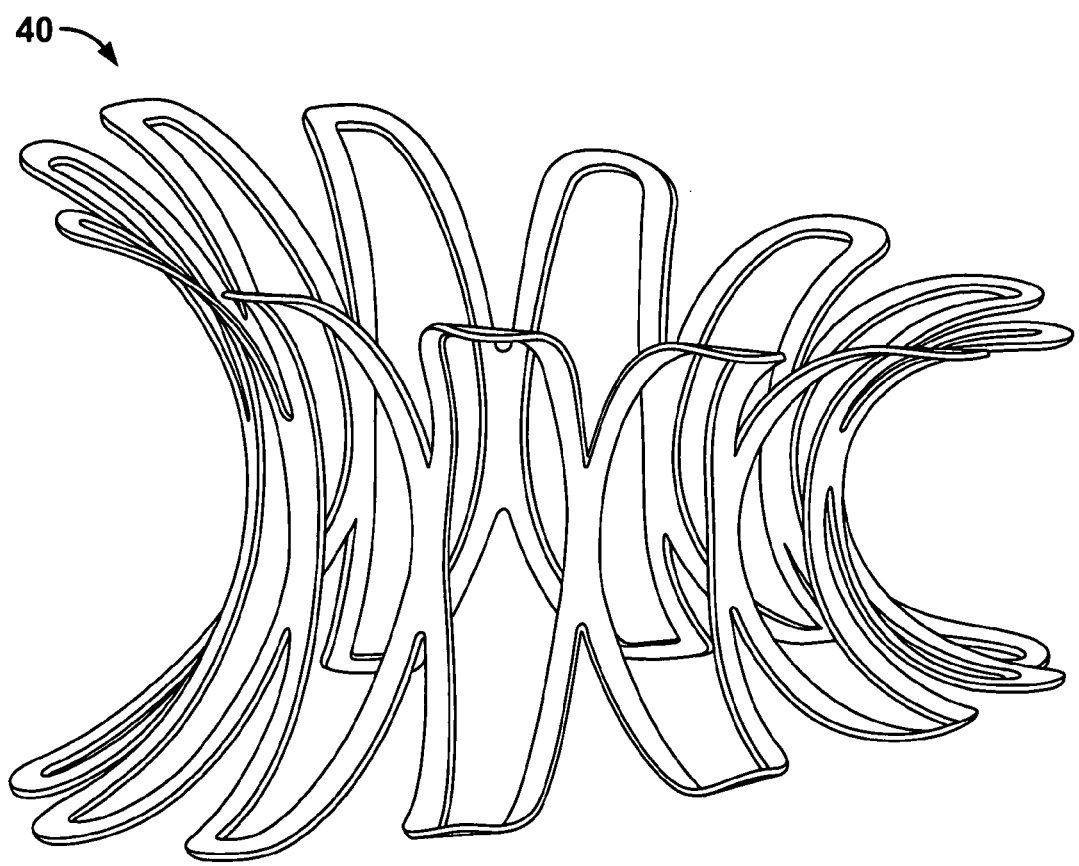
FIG. 25 is generally similar to FIG. 24 for still another illustrative embodiment of a component for a prosthetic heart valve in accordance with the invention.
Figure 26:
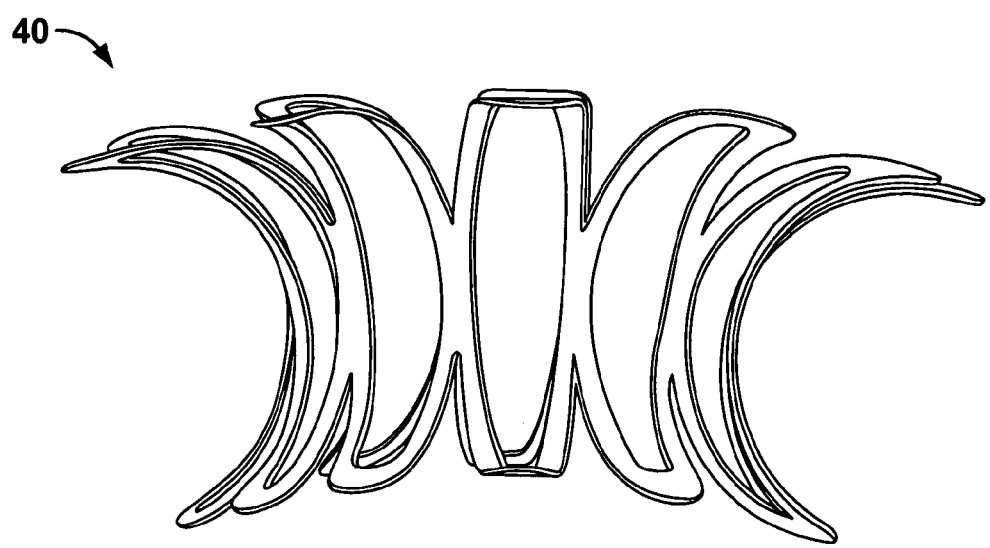
FIG. 26 is a simplified elevational view of yet another illustrative embodiment of a component for a prosthetic heart valve in accordance with the invention.

FIGS. 25 and 26 show other variations in the shape of annular structure 40 that can allow for better conformance to the mitral valve anatomy. For example, FIG. 25 shows an asymmetric shape, while FIG. 26 shows a symmetric saddle shape.

Figure 27:
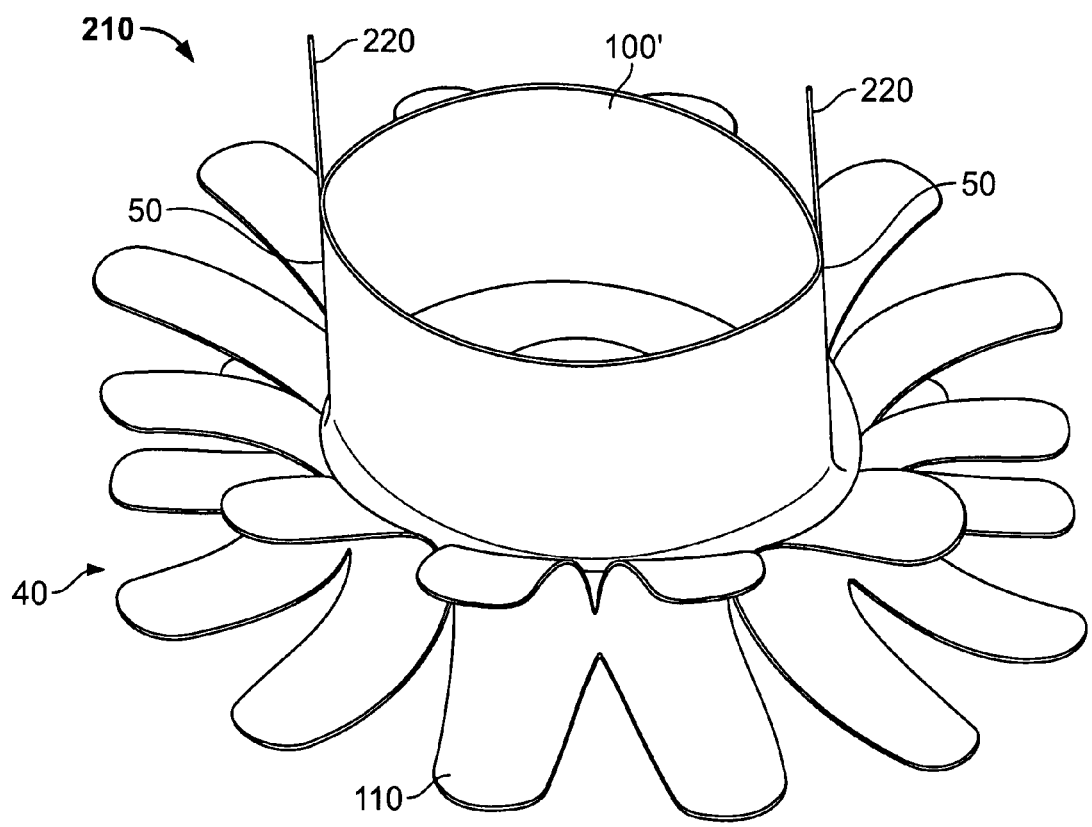
FIG. 27 is a simplified perspective view of still another illustrative embodiment of a prosthetic heart valve in accordance with the invention.

FIG. 27 shows that a valve 210 with an elliptical shape may also conform better to the mitral valve anatomy than a circular-shaped valve. Additionally, instead of a tri-leaflet design, FIG. 27 shows that a bi-leaflet design 100' can be used (leaflets shown open in FIG. 27). Once again, chordae 220 can be attached at commissure posts 50, and the edge of cuff 110 can be contoured to follow the edge of stent 40.

Although the structures shown in FIGS. 18-27 are described primarily as mitral valve structures, it will be understood that this is only illustrative, and that various structures and principles illustrated by or in these FIGS. can be employed in other types of prosthetic heart valves (e.g., in prosthetic aortic valves).

Briefly recapitulating some of what has been said in somewhat different terms, it will be seen that in many embodiments of the invention, at least the portion 40 of the prosthetic valve that goes in the patient's native valve annulus includes an annular array of generally diamond-shaped cells 46. Upstream apex portions 144 of at least some of these cells are resiliently biased to deflect radially outwardly from at least some other portions of structure 40. Downstream apex portions 142 of at least some of these cells are similarly resiliently biased to deflect radially outwardly from at least some other portions of structure 40. This allows the valve to clamp tissue of the patient between the upstream and downstream apex portions that thus deflect outwardly.

Each of the above-mentioned apex portions comprises two spaced-apart members that join at an apex of that apex portion. For example, in FIG. 7 the two spaced-apart members of one representative downstream apex portion are identified by reference letters b and c, and the apex where those members join is identified by reference letter a.

Still more particularly, the resiliently biased, radially outward deflection of each upstream apex portion 144 typically includes a downstream component of motion of that upstream apex portion (in addition to a radially outward component of motion). This is illustrated, for example, by the arcuate arrows 44 in FIGS. 1-3. Similarly, the resiliently biased, radially outward deflection of each of downstream apex portion 142 typically includes an upstream component of motion of that downstream apex portion (in addition to a radially outward component of motion). This is illustrated, for example, by the arcuate arrows 42 in FIGS. 1-3. The result of this is that the upstream and downstream apex portions begin as jaws that are relatively far apart and wide open. They then effectively pivot toward one another to clamp tissue therebetween.

References herein to an annular perimeter of a structure being changeable in length mean that the perimeter increases or decreases in size without going through any major topological change. In other words, the shape of the structure remains basically the same, and only the perimeter size changes. For example, the shape may be always basically circular. There is no folding or wrapping of the structure to change its perimeter size. The shape either basically shrinks down or expands out. A minor exception to the foregoing is that ellipses and circles are regarded herein as having the same basic topology. Thus an ellipse may shrink to a circle, for example, without that constituting "a major topological change."

It will be understood that the foregoing is only illustrative of the principles of the invention, and that various modifications can be made by those skilled in the art without departing from the scope and spirit of the invention. For example, the particular patterns of stent cells like 22 and 46 shown herein are only illustrative, and many other stent configurations can be used instead if desired. It will be appreciated that the valves of this invention can, if desired, be implanted in a patient less invasively. For example, the valves of this invention can be implanted percutaneously, trans-apically, or surgically, and with or without resected and/or debrided leaflets. Depending on the embodiment, the valve can be collapsed in a variety of configurations before deployment in a single- or multi-stage process. Access can be achieved, for example, through the femoral artery, abdominal aorta, or the apex of the heart.

The invention claimed is:

1. A prosthetic heart valve comprising:
an annular structure having an annular perimeter that is changeable in length between (1) a first relatively small length suitable for delivery of the valve into a patient with reduced invasiveness, and (2) a second relatively large length suitable for use of the annular structure to engage tissue of the patient adjacent to the patient's native aortic valve annulus and also in the patient's aorta, the annular structure including an annularly continuous annulus portion adapted for implanting adjacent the patient's native aortic valve annulus upstream from the ostia of the patient's coronary arteries, and an annularly continuous aortic portion adapted for implanting in the patient's aorta, the annulus portion and the aortic portion being connected to one another only by a plurality of linking structures, the annulus portion and the aortic portion each including an annular array of diamond-shaped cells, each cell having an upstream apex portion directly connected to a downstream apex portion at connection points, the upstream apex portion having an upstream apex aligned with a downstream apex of the downstream apex portion in a longitudinal direction of the annular structure, each of the linking structures having a first end connected directly to the upstream apex of one of the cells in the aortic portion, the first ends being spaced from one another in an annular direction of the aortic portion, and each of the linking structures having a second end connected to the cells in the annulus portion, the second ends being spaced from one another in an annular direction of the annulus portion;
a cuff extending annularly around the annulus portion and having a first annular edge positioned downstream of the upstream apices and a second annular edge positioned upstream of the downstream apices; and
a flexible leaflet structure attached to the annular structure, wherein
the upstream apex portion of each cell in a group of the cells in the annulus portion is resiliently biased to deflect radially outwardly from the connection points, and the downstream apex portion of each cell in the group of the cells is resiliently biased to deflect radially outwardly from the connection points,
whereby each cell in the group of the cells, in use, clamps tissue of the patient adjacent to the patient's native valve annulus between the upstream apex portion of the cell and the downstream apex portion of the cell, with the upstream apex portion of the cell engaging tissue upstream from the native valve annulus and the downstream apex portion of the cell engaging tissue downstream from the native valve annulus.

2. The valve defined in claim 1 wherein the annular perimeter is elastically changeable in length between the first relatively small length and the second relatively large length.

3. The valve defined in claim 1, wherein
the resiliently biased, radially outward deflection of each of the upstream apex portions includes a downstream component of motion by the upstream apex portion, and
the resiliently biased, radially outward deflection of each of the downstream apex portions includes and upstream component of motion by the downstream apex portion.

4. The valve defined in claim 1 further comprising a plurality of commissure post members that are cantilevered from the annulus portion.

5. The valve defined in claim 4 wherein the commissure post members are spaced circumferentially around the annulus portion so that they can be aligned with respective commissures of the patient's native aortic valve.

6. The valve defined in claim 4 wherein the linking structures consist essentially of a respective pair of struts associated with each of the commissure post members, the struts in each pair extending along respective opposite sides of the associated commissure post members to the aortic portion, each pair of struts including a first strut having an end connected to a first cell in the aortic portion and a second strut having an end connected to a second cell in the aortic portion different from the first cell.

7. The valve defined in claim 1 wherein the diamond-shaped cells of the aortic portion each defines an area larger than an area of each diamond-shaped cell of the annulus portion.

8. The valve defined in claim 1, wherein each of the upstream apices includes a barb.

9. The valve defined in claim 8, wherein each of the downstream apices includes a barb.

10. The valve defined in claim 1, wherein the annulus portion includes at least one annular row of cells, and the group of cells includes less than all of the cells in the annular row.

11. A prosthetic heart valve comprising:

an annularly compressible and expandable annular structure including (1) an annularly continuous annulus inflow portion adapted for implanting adjacent a patient's native aortic valve annulus, (2) an annularly continuous aortic outflow portion adapted for implanting in the patient's aorta, and (3) a plurality of linking structures connecting the annulus inflow portion to the aortic outflow portion, each of the linking structures having a first end connected directly to the aortic outflow portion, the first ends being spaced from one another in an annular direction around the annular structure, the annulus inflow portion defining a plurality of commissure tips that are spaced from one another in the annular direction, each of the commissure tips having a free end and an associated pair of the linking structures disposed on opposite sides of the commissure tip in the annular direction, the associated pair of linking structures including a first linking structure and a second linking structure, the first linking structure and the second linking structure being spaced apart from one another by a distance in the annular direction that is less than the distance in the annular direction between the first linking structure and a next adjacent linking structure not in the pair such that the second linking structure is not between the first linking structure and the next adjacent linking structure, the annulus portion including an annular array of diamond-shaped cells, each cell having an upstream apex portion directly connected to a downstream apex portion at connection points, the upstream apex portion having an upstream apex aligned with a downstream apex of the downstream apex portion in a longitudinal direction of the annular structure; and a flexible leaflet structure attached to the annular structure, wherein the upstream apex portion of each cell in a group of the cells is resiliently biased to deflect radially outwardly from the connection points, and the downstream apex portion of each cell in the group of the cells is resiliently biased to deflect radially outwardly from the connection points, whereby each cell in the group of the cells, in use, clamps tissue of the patient adjacent to the patient's native valve annulus between the upstream apex portion of the cell and the downstream apex portion of the cell.

12. The prosthetic heart valve defined in claim 11, wherein an edge of the annulus inflow portion that is most remote from the aortic outflow portion includes a recessed edge portion aligned in the longitudinal direction of the annular structure with at least one of the commissure tips, the recessed edge portion being closer to the aortic outflow portion than other portions of the edge of the annulus inflow portion.

13. A prosthetic heart valve comprising:

an annular structure having an annular perimeter that is changeable in length between (1) a first relatively small length suitable for delivery of the valve into a patient with reduced invasiveness, and (2) a second relatively large length suitable for use of the annular structure to engage tissue of the patient adjacent to the patient's native aortic valve annulus and also in the patient's aorta, the annular structure including an annularly continuous annulus portion adapted for implanting adjacent the patient's native aortic valve annulus upstream from the ostia of the patient's coronary arteries, an annularly continuous aortic portion adapted for implanting in the patient's aorta, and a plurality of commissure post members cantilevered from the annulus portion, the annulus portion and the aortic portion being connected to one another only by a plurality of linking structures, the annulus portion and the aortic portion each including an annular array of diamond-shaped cells, each cell having an upstream apex portion directly connected to a downstream apex portion at connection points, the upstream apex portion having an upstream apex aligned with a downstream apex of the downstream apex portion in a longitudinal direction of the annular structure, each of the linking structures having a first end connected directly to the upstream apex of one of the cells in the aortic portion, the first ends being spaced from one another in an annular direction of the aortic portion, and each of the linking structures having a second end connected directly to one of the commissure post members, the second ends being spaced from one another in an annular direction of the annulus portion;

a cuff extending annularly around the annulus portion and having a first annular edge positioned downstream of the upstream apices and a second annular edge positioned upstream of the downstream apices; and a flexible leaflet structure attached to the annular structure, wherein the upstream apex portion of each cell in a group of the cells in the annulus portion is resiliently biased to deflect radially outwardly from the connection points, and the downstream apex portion of each cell in the group of the cells is resiliently biased to deflect radially outwardly from the connection points, whereby each cell in the group of the cells, in use, clamps tissue of the patient adjacent to the patient's native valve annulus between the upstream apex portion of the cell and the downstream apex portion of the cell, with the upstream apex portion of the cell engaging tissue upstream from the native valve annulus and the downstream apex portion of the cell engaging tissue downstream from the native valve annulus.

14. The valve defined in claim 13, wherein the first end of each of the linking structures connects to the aortic portion at a point that is axially aligned with the commissure post member from which that linking structure extends.

15. The valve defined in claim 13, wherein the linking structures include a respective pair of struts associated with each of the commissure post members, the struts in each pair extending along respective opposite sides of the associated commissure post member to the aortic portion, each pair of struts including a first strut having an end connected to a first cell in the aortic portion and a second strut having an end connected to a second cell in the aortic portion different from the first cell.

* * * * *